United States Patent
Aggarwal et al.

(10) Patent No.: US 7,945,305 B2
(45) Date of Patent: May 17, 2011

(54) ADAPTIVE ACQUISITION AND RECONSTRUCTION OF DYNAMIC MR IMAGES

(75) Inventors: Nitin Aggarwal, Champaign, IL (US); Saptarshi Bandyopadhyay, Champaign, IL (US); Yoram Bresler, Urbana, IL (US)

(73) Assignee: The Board Of Trustees Of The University of Illinois, Urbana, IL (US)

( * ) Notice: Subject to any disclaimer, the term of this patent is extended or adjusted under 35 U.S.C. 154(b) by 685 days.

(21) Appl. No.: 11/217,805

(22) Filed: Sep. 1, 2005

(65) Prior Publication Data

US 2006/0224062 A1 Oct. 5, 2006

Related U.S. Application Data

(60) Provisional application No. 60/671,302, filed on Apr. 14, 2005.

(51) Int. Cl.
*A61B 5/05* (2006.01)

(52) U.S. Cl. ......... 600/413; 600/407; 600/410; 600/436

(58) Field of Classification Search ........... 600/407–480
See application file for complete search history.

(56) References Cited

U.S. PATENT DOCUMENTS

| | | | |
|---|---|---|---|
| 4,567,893 A | 2/1986 | Charles et al. | |
| 4,663,591 A | 5/1987 | Pelc et al. | |
| 4,706,026 A | 11/1987 | Pelc et al. | |
| 4,937,526 A | 6/1990 | Ehman et al. | |
| 5,539,312 A * | 7/1996 | Fu et al. ........................ | 324/309 |
| 5,766,128 A * | 6/1998 | Halamek et al. ............... | 600/410 |
| 6,230,040 B1 * | 5/2001 | Wang et al. .................... | 600/415 |
| 6,275,040 B1 * | 8/2001 | Zur ................................. | 324/320 |
| 6,587,707 B2 | 7/2003 | Nehrke et al. | |
| 6,704,593 B2 | 3/2004 | Stainsbv et al. | |
| 6,708,052 B1 | 3/2004 | Mao et al. | |
| 6,754,521 B2 * | 6/2004 | Prince ........................... | 600/420 |
| 6,950,543 B2 * | 9/2005 | King et al. .................... | 382/128 |
| 7,245,124 B2 * | 7/2007 | Shu et al. ...................... | 324/307 |
| 7,330,027 B2 * | 2/2008 | Kozerke et al. ............... | 324/307 |
| 2002/0010397 A1 * | 1/2002 | Prince ........................... | 600/420 |
| 2003/0206648 A1 * | 11/2003 | King et al. .................... | 382/128 |
| 2004/0210130 A1 * | 10/2004 | Prince ........................... | 600/420 |
| 2006/0183999 A1 * | 8/2006 | Lorenz et al. ................. | 600/410 |
| 2006/0226836 A1 * | 10/2006 | Shu et al. ...................... | 324/309 |

OTHER PUBLICATIONS

Qi Zhao, Optimal Adaptive Dynamic MRI Based on Time Sequential Sampling Theory, Thesis, University of Illinois at Urbana-Champaign, 2002.
Qi Zhao, Dynamic Imaging of Time-Varying Objects, Proc. Intl. Soc. Mag. Reson. Med 9 (2001).

(Continued)

*Primary Examiner* — Brian Casler
*Assistant Examiner* — Nasir Shahrestani
(74) *Attorney, Agent, or Firm* — Quarles & Brady LLP

(57) ABSTRACT

A method for acquiring MR data from a beating heart during subject respiration includes a prescan phase in which a respiratory compensation table and a k-space sampling schedule are produced. The k-space sampling table is produced using a spatio-temporal model of the beating heart and time sequential sampling theory. During the subsequent scan an imaging pulse sequence which is prospectively compensated for respiratory motion is used to acquire k-space data from the subject. The imaging pulse sequence is repeated to play out the phase encodings in the order listed in the k-space sampling schedule.

28 Claims, 22 Drawing Sheets

OTHER PUBLICATIONS

Nitin Aggarwal, et al, Spatio-Temporal Modeling and Adaptive Acquisition for Cardiac MRI, 2004 IEEE, 628631.

Yoram Bresler, Fast Acquisition and Sampling in MRI: Introduction to Time-Sequential Sampling of Spatio-Temporal Signals, 2002 IEEE, 713-716.

N. Parker Willis, Lattice-Theoretic Analysis of Time-Sequential Sampling of Spatiotemporal Signals—Part 1, IEEE Trans. on Info. Theory, vol. 43, No. 1, Jan. 1997.

Raymond Y. Kwong, et al, Detecting Acute Coronary Syndrome in the Emergency Department With Cardiac Mag. Reson. Imaging, www.circulationaha.org, 531-537.

Nitin Aggarwal et al, A Time-Warped Spectral Model for Minimum Redundancy Sampling in Cardiac Imaging, Proc. Intl. Soc. Mag. Reson. Med. 10 (2002).

Qi Zhao, et al, Dynamic Magnetic Resonance Imaging Based on Optimal Sampling and Time-Varying Harmonic Model, Proc. Intl. Soc. Mag. Reson. Med. 10 (2002).

Nitin Aggarwal, et al, Spatio-Temporal Modeling and Minimum Redundancy Adaptive Acquisition in Dynamic MRI, IEEE 2002, 737-740.

* cited by examiner

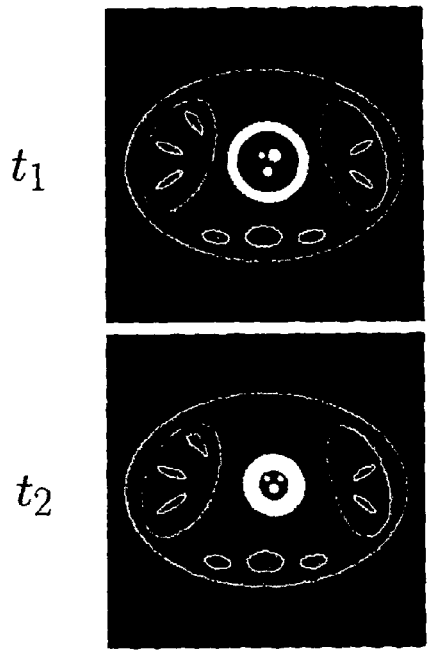
FIG. 20(A)
$t_1$
$t_2$
$J(\mathbf{r}, t)$
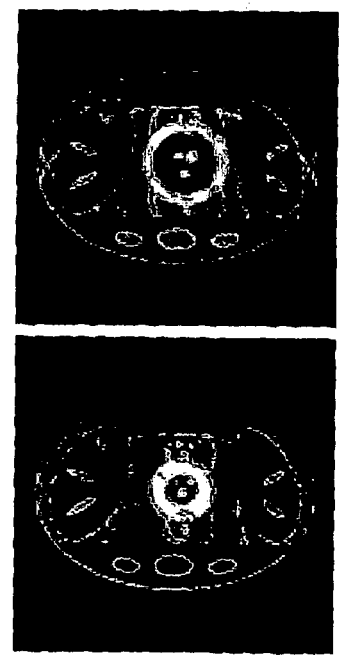
$t_1$
FIG. 20(B) $t_2$
$\hat{J}_{TS}(\mathbf{r}, t)$ FIG. 20(C)
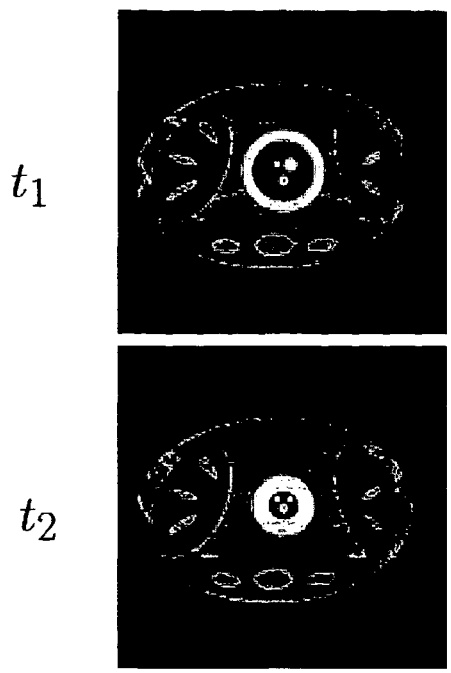
$t_1$
$t_2$
$\hat{I}_{ACTS}(\mathbf{r}, t)$
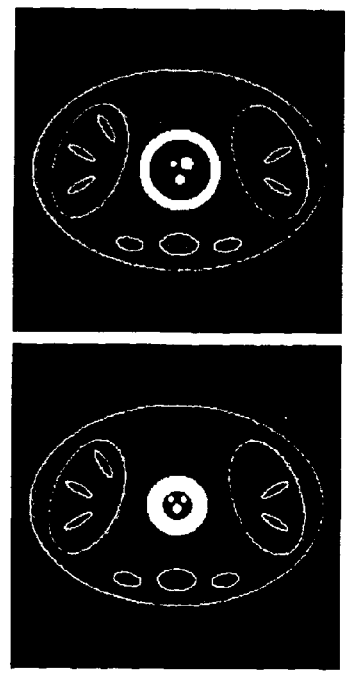
$t_1$
$t_2$
FIG. 20(D)
$I(\mathbf{r}, t)$ FIG. 21(A)
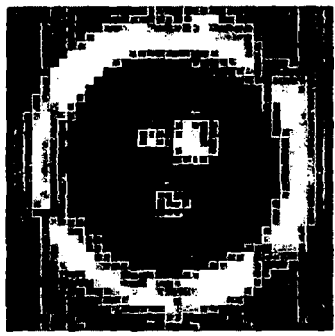
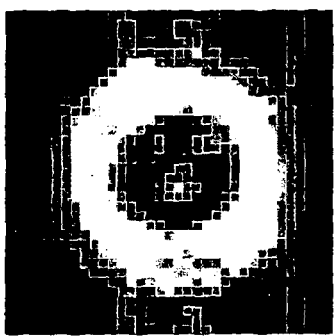
$\hat{J}_{TS}(\mathbf{r}, t)$
FIG. 21(B)
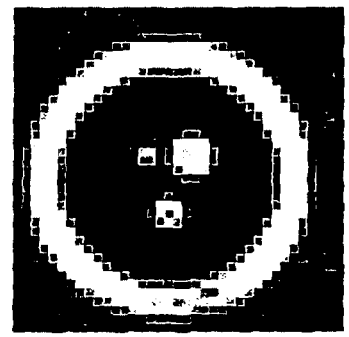
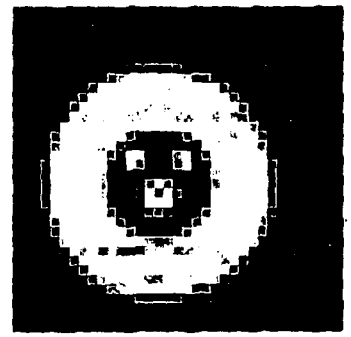
$\hat{I}_{ACTS}(\mathbf{r}, t)$

ADAPTIVE ACQUISITION AND RECONSTRUCTION OF DYNAMIC MR IMAGES

CROSS-REFERENCE TO RELATED APPLICATIONS

This application is based on U.S. Provisional Patent Application Ser. No. 60/671,302 filed on Apr. 14, 2005 and entitled "Adaptive Acquisition And Reconstruction Of Dynamic MR Images".

STATEMENT REGARDING FEDERALLY SPONSORED RESEARCH

This invention was made with government support under contract Number BES02-01879 awarded by the National Science Foundation and Grant No. R21HL62336-02 awarded by the National Institute of Health. The United States Government has certain rights in this invention.

BACKGROUND OF THE INVENTION

The field of the invention is magnetic resonance imaging methods and systems. More particularly, the invention relates to methods for MR imaging of dynamically moving objects, such as the beating heart, at a high-spatial and temporal-resolution.

Any nucleus which possesses a magnetic moment attempts to align itself with the direction of the magnetic field in which it is located. In doing so, however, the nucleus precesses around this direction at a characteristic angular frequency (Larmor frequency) which is dependent on the strength of the magnetic field and on the properties of the specific nuclear species (the magnetogyric constant * of the nucleus). Nuclei which exhibit this phenomena are referred to herein as "spins".

When a substance such as human tissue is subjected to a uniform, static magnetic field (polarizing field $B_0$), the individual magnetic moments of the spins in the tissue attempt to align with this polarizing field, but precess about it in random order at their characteristic Larmor frequency. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$, which is rotating, or spinning, in the x-y plane at the Larmor frequency. The practical value of this phenomenon resides in the signal that is emitted by the excited spins after the excitation signal $B_1$ is terminated. There are a wide variety of measurement sequences in which this nuclear magnetic resonance ("NMR") phenomenon is exploited.

When utilizing NMR to produce images, a technique is employed to obtain NMR signals from specific locations in the subject. Typically, the region that is to be imaged (region of interest) is scanned by a sequence of NMR measurement cycles which vary according to the particular localization method being used. The resulting set of received NMR signals, or "views", are digitized and processed to reconstruct the image using one of many well known reconstruction techniques. To perform such a scan, it is, of course, necessary to elicit NMR signals from specific locations in the subject. This is accomplished by employing magnetic fields ($G_x$, $G_y$, and $G_z$) that have the same direction as the polarizing field B0, but which have a gradient along the respective x, y and z axes. By controlling the strength of these gradients during each NMR cycle, the spatial distribution of spin excitation can be controlled and the location of the resulting NMR signals can be identified.

The present invention will be described in detail with reference to a variant of the Fourier transform (FT) imaging technique, which is frequently referred to as "spin-warp". The spin-warp technique is discussed in an article entitled "Spin Warp NMR Imaging and Applications to Human Whole-Body Imaging" by W. A. Edelstein et al., Physics in Medicine and Biology, Vol. 25, pp. 751-756 (1980). It employs a variable amplitude phase encoding magnetic field gradient pulse prior to the acquisition of NMR spin-echo signals to phase encode spatial information in the direction of this gradient. In a two-dimensional implementation (2DFT), for example, spatial information is encoded in one direction by applying a phase encoding gradient ($G_y$) along that direction, and then a signal is acquired in the presence of a readout magnetic field gradient ($G_x$) in a direction orthogonal to the phase encoding direction. The readout gradient present during the acquisition encodes spatial information in the orthogonal direction. In a typical 2DFT pulse sequence, the magnitude of the phase encoding gradient pulse Gy is incremented ($\Delta G_y$) in the sequence of views that are acquired during the scan to produce a set of NMR data from which an entire image can be reconstructed.

Object motion during the acquisition of NMR image data produces both blurring and "ghosts". Ghosts are particularly apparent when the motion is periodic, or nearly so. For most physiological motion each view of the NMR signal is acquired in a period short enough that the object may be considered stationary during the acquisition window. In such case the blurring and ghosting is due to the inconsistent appearance of the object from view to view. Motion that changes the appearance between views such as that produced by a subject moving, by the respiration or the cardiac cycle, or by peristalsis, is referred to hereinafter as "view-to-view motion". Motion may also change the amplitude and phase of the NMR signal as it evolves during the pulse sequence and such motion is referred to hereinafter as "in-view motion".

Both blurring and ghosting can be reduced if the data acquisition is synchronized with the functional cycle of the object to reduce view-to-view motion. This method is known as gated NMR scanning, and its objective is to acquire NMR data at the same point during successive functional cycles so that the object "looks" the same in each view. The drawback of gating is that NMR data may be acquired only during a small fraction of the object's functional cycle, and even when the shortest acceptable pulse sequence is employed, the gating technique can significantly lengthen the data acquisition. Also, if the object motion does not repeat exactly from cycle-to-cycle, the reconstructed images represent the object time-averaged over several such cycles during which the data was acquired, rather than the object and its true dynamics. Furthermore, the imperfect cycle-to-cycle repetition results in residual view-to-view motion and image artifacts.

Another method for eliminating ghost artifacts is disclosed in U.S. Pat. No. 4,567,893, issued on Feb. 4, 1986. This prior patent teaches that the distance in the image between the ghosts and the object being imaged is maximized when the NMR pulse sequence repetition time is an odd multiple of one-fourth of the duration of the periodic signal variation. This can be used to alleviate ghosts due to respiratory motion. While this method, indeed, improves image quality, it does impose a constraint on the NMR pulse sequence repetition time and it often results in a longer total scan time. It also assumes that the motion is periodic.

Yet another method for reducing the undesirable effects due to periodic signal variations is disclosed in U.S. Pat. No. 4,706,026 issued on Nov. 10, 1987 and entitled "A Method For Reducing Image Artifacts Due To Periodic Variations In NMR Imaging." In one embodiment of this method, an assumption is made about the signal variation period (e.g. due, for example, to subject respiration) and the view order is altered from the usual monotonically increasing phase-encoding gradient to a pre-selected view order. For a given signal variation period, a view order is chosen so as to make the NMR signal variation as a function of the phase-encoding amplitude be at a desired frequency. In one embodiment, the view order is selected such that the variation period appears to be equal to the total NMR scan time (low frequency) so that the ghost artifacts are brought as close to the object being imaged as possible. In another embodiment (high frequency), the view order is chosen to make the variation period appear to be as short as possible so as to push the ghost artifacts as far from the object as possible.

This prior method is effective in reducing artifacts, and is in some respects ideal if the variation is rather regular and at a known frequency. On the other hand, the method is not very robust if the assumption made about the motion temporal period does not hold (e.g., because the subject's breathing pattern changes or is irregular). If this occurs, the method loses some of its effectiveness because the focusing of the ghosts, either as close to the object or as far from the object as possible, becomes blurred. A solution to this problem is disclosed in U.S. Pat. No. 4,663,591 which is entitled "A Method For Reducing Image Artifacts Due To Periodic Signal Variations in NMR Imaging." In this method, the non-monotonic view order is determined as the scan is executed and is responsive to changes in the period so as to produce a desired relationship (low frequency or high frequency) between the signal variations and the gradient parameter. The effectiveness of this method, of course, depends upon the accuracy of the means used to sense the subject motion, and particularly, any variations in the periodicity of that motion.

Imaging the heart is a particularly challenging problem. The heart itself is in motion (cardiac motion) and overlying this motion is translational, rotational and compressive motion due to breathing (respiratory motion). In certain applications, like imaging of the head or knees, it is often possible to limit the motion by asking the subject to voluntarily hold still or by using physical restraints to immobilize the part being imaged. However, for applications like cardiac imaging, it is not possible to eliminate the motion during the time period of MR data acquisition. Hence, for such applications it is necessary to develop methods for acquiring MR images in the presence of physiological motion. Also, capturing "snapshot" images of the heart is much different than acquiring a dynamic movie of the heart. Whereas in the first case motion may be compensated for, in the second motion is to be recovered. For either goal so-called "retrospective" motion correction methods may be used after the NMR data is acquired, or "prospective" motion compensation methods may be used to adapt the MR data acquisition itself to compensate or capture the motion.

Breathholding and respiratory and cardiac gating methods are often used to reduce image artifacts in cardiac images. Such methods are effective, but they substantially increase the total scan time and with some subjects they simply cannot be used.

A number of retrospective methods have been proposed for correcting the acquired MR data to suppress the effects of subject motion. These methods typically assume a simple model for respiratory motion for example, rigid translation in 1 or 2 dimensions, rotational motion, expansion motion, etc. MR (or other sensory) "navigator" data may be acquired to estimate the respiration-induced motion parameters. As described for example, in U.S. Pat. Nos. 4,937,526 and 5,539, 312, this estimate is then used to compensate for the motion during image reconstruction. These methods typically do not capture the complexity of the respiratory motion or do not accurately compensate for the complex motion.

Methods such as that disclosed in U.S. Pat. No. 6,587,707 have also been developed for prospectively correcting for motion. Such methods assume that the motion can be modeled as translation and/or rotation and then they modify the MRI pulse sequence to compensate for the estimated motion. Such models typically do not account for the considerable non-rigid deformation of the heart that occurs during respiration and residual motion artifacts occur.

As disclosed in the University of Illinois Master of Science Thesis of Qi Zhao published in 2002 and titled "Optimal Adaptive Dynamic MRI Based On time Sequential Sampling Theory," a spatio-temporal model of cardiac motion has been developed and used to prospectively adapt the MR data acquisition k-space sampling scheme such that cardiac motion artifacts are suppressed. This technique is very effective, but it requires that k-space be sampled according to a prescribed temporal pattern and this precludes the simultaneous use of many respiratory motion artifact suppression methods, such as respiratory gating or windowing.

SUMMARY OF THE INVENTION

The present invention is a method for acquiring MR images of dynamic objects based on adaptation of the MR data acquisition and reconstruction to a model of the motion and dynamics of the object. The method is applicable to free-breathing cardiac imaging in which image artifacts caused by both respiratory motion and cardiac motion need to be suppressed. Motion of the heart (and surrounding tissue) due to respiration is correlated to measurable parameters such as diaphragm position, and during the acquisition of image data this parameter is measured and used along with the motion and dynamics model to alter the data acquisition such that the acquired image data is prospectively compensated for respiratory motion. An optimal time-sequential k-space sampling schedule is produced based on MR data acquired during a prescan and this sampling schedule, adapted to handle respiratory motion, is employed to acquire image data which is used in conjunction with a model for cardiac dynamics to reconstruct high-temporal and high spatial resolution images of the beating heart.

BRIEF DESCRIPTION OF THE DRAWINGS

FIGS. 20A-20D show the results of the numerical experiment with the software phantom using the non-affine respiratory motion field illustrated in FIG. 18;

FIGS. 21A and 21B show the details of the reconstruction of the central (cardiac) region for the reconstructions shown in FIG. 19.

GENERAL DESCRIPTION OF THE INVENTION

Figure 1:
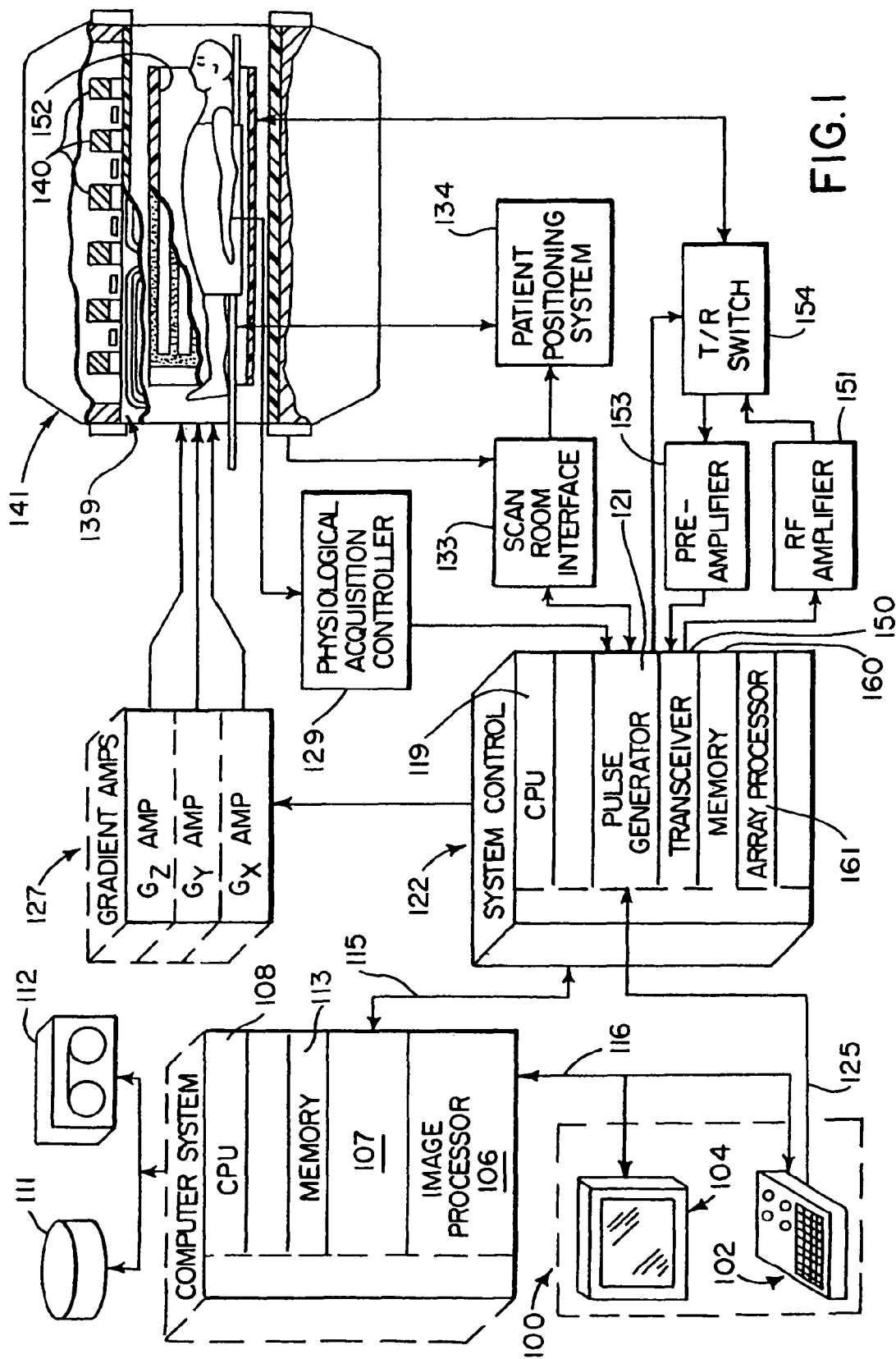
FIG. 1 is a block diagram of an MRI system that employs the present invention.

In one embodiment, the present invention enables high resolution cardiac images or cine to be acquired while the subject is breathing, without triggering or synchronization of MR acquisition to either ECG or respiration. The MR data acquisition is adapted to the respiratory motion of the subject being imaged, in order to offset the effect of the motion on the acquired NMR signals. This respiratory motion correction method is based on a complex model of heart translation, rotation and compression caused by the subject's breathing. The method can also be used to image other parts of the anatomy affected by cardiac, respiratory or other motion in humans or animals. For simplicity and concreteness, we refer to the cardiac imaging application in the sequel.

Used concurrently with the respiration correction method is an adaptive minimum redundancy k-space sampling method that is optimized for the cardiac motion of the particular subject being imaged. Data acquired according to this optimized k-space sampling sequence schedule is used in conjunction with a model of cardiac dynamics to reconstruct a high-temporal and high-spatial resolution movie of the beating heart.

In the following description, the Time-Varying Image (TVI) being acquired is denoted variously by $I(r,t)$, $J(r,t)$ and $H(r,t)$; where r is the d-dimensional (d=2,3) spatial variable. Fourier transforms of signals are indicated by the variables used, e.g., $I(k_x, y, f)$ is the Fourier transform of $I(x, y, t)$ w.r.t. x and t; $k_x$ and f refer to the spatial-frequency (w.r.t x) and temporal frequencies, respectively.

CARDIAC MODEL: The idea behind using a cardiac model is to incorporate information about the spatial and temporal dynamics of the beating heart into the MR data acquisition and reconstruction process. By adjusting the model parameters to the observed characteristics of the subject's heart, we can adapt the MR imaging process to the particular subject being imaged. For instance, denoting a dynamic model parameterized by a set of parameters $\alpha$ by $M(\alpha)$, our imaging scheme (in the absence of respiratory motion) proceeds as follows:

I. Dynamic Model Acquisition: At this prescan step we acquire MR and/or auxiliary data (e.g. ECG signal from the subject) in order to adapt the model parameters to the particular subject being imaged. We denote the optimal set of parameters found at this stage by $\alpha^*$.

II. Design of Sampling Schedule: We next design the sampling schedule (i.e. the specifications of the MR data that is to be acquired and its timing) by solving an optimization problem of the following form:

$$\Psi^* = \underset{\Psi}{\operatorname{argmin}} \varepsilon [Q(M(\alpha^*), \Psi), \Psi] \qquad \text{Eq. (1)}$$

where in Eq. (1), Q is a measure of the expected quality of the reconstruction that may depend upon our model of the object being imaged and the sampling schedule we use to acquire this data; and $\varepsilon$ is our imaging cost function that penalizes for loss in image quality as well as properties of the sampling schedule (for instance, total acquisition time, specific absorption rate (SAR), repetition time requirement, etc.)

III. Scanning: We then acquire MR data as prescribed by the optimal sampling schedule designed at the previous step.

IV. Image Reconstruction: Finally MR image (or cine) is reconstructed from the acquired data using information provided by the model $M(\alpha^*)$ of the object being imaged.

Various classes of dynamic models can be used in the general method described above. We, next, discuss models based on the Dual-k-t (DKT) support of the cardiac TVI. For spinwarp imaging, the DKT support for a cardiac TVI $I(r,t)$ (in the absence of respiratory motion) is defined as $\beta_I \triangleq \text{supp} \{I(r,t)\}$. (Recall that the support of a function defined on a domain D is the set of points in D at which the function is non-zero). Because the spectral support of an object of a finite extent (in either space or time) is infinite, we use instead the essential support, which contains a sufficient fraction of the energy, or other desired measure of concentration of the function. Later in this section we will discuss examples of other cardiac models such as the "Time-Varying Harmonic Model" and the "Time Varying Banded Spectral Model".

For concreteness, we now introduce a particular DKT support model, referred to as the "Banded Spectral Model". This model characterizes the cardiac TVI (in the absence of respiratory motion), $I(r,t)$, by its DKT support $\beta_I$ of the form shown in FIG. 4. This model captures the following characteristics of the dynamic object: (1) the finite spatial field-of-view (FOV)

outside which the function is zero; (2) the approximate periodicity of the cardiac motion reflected in the quasi-harmonic banded temporal spectrum with frequency spacing determined by the heart-rate; and (3) the spatial localization of the fast motion to the heart region defining the dynamic field-of-view (D-FOV).

DETERMINING CARDIAC DYNAMICS MODEL PARAMETERS: As outlined above, before imaging the object we estimate the parameters used to model the spatial and temporal dynamics of the object using MR and/or auxiliary data (like ECG). For example, for the Banded Spectral Model, we need to determine the number and widths of harmonic bands along with the total and dynamic field-of-view (FOV and D-FOV) of the imaged object. As elaborated for the preferred embodiment, this is done through an automated prescan procedure called Dynamic Model Acquisition.

CARDIAC MODEL-ADAPTED MRI ACQUISITION AND RECONSTRUCTION: An MR acquisition schedule includes specification of the order and time instants at which k-space samples are acquired. We consider MR acquisition schedules that satisfy the following two properties; (P1) an alias-free reconstruction of the object can be obtained from the acquired data, subject to the modeling assumptions; (P2) the acquisition scheme is time-sequential (TS) i.e. at any given time instant only a single view of the object is obtained (for example data along a single line, curve, or plane in k-space is acquired). Data acquired within a time interval in which object motion can be neglected is considered to be a single time-instant for our purpose.

For any given -DKT support model, several such sampling schemes may exist (in theory, though some of them may be impractical due to hardware or other constraints). To reduce the requirements on the MR hardware and SAR, we choose the eligible MR acquisition scheme that minimizes the requirement on the sampling speed. The design method uses the DKT support of the object and produces an optimal TS sampling schedule $\Psi^{TS} = \{k^{TS}(n), nT_R\}_n$; where $k^{TS}(n)$ is the set of k-space locations sampled at time $nT_R$. For MR imaging of 2D slices, the sampling schedule also specifies which slice is selected at each of the sampling time instants.

Note that the same k-space location may be sampled multiple times at different acquisition time instants. The number of times that the same k-space point is sampled may depend on several factors including: the accuracy needed in the reconstructed image; the shape of the dual-k-t support (e.g., the width of the bands in a banded model), and limits on the total acquisition time.

We can design the TS sampling schedule so that it contains gaps, i.e. for some integer values of n, we do not sample any location in k-space, while still being able to reconstruct the TVI (at same temporal and spatial resolution) from the acquired data-set. These gaps in the TS sampling schedule can be used instead to acquire auxiliary navigator data, for example navigator data that is used to estimate respiratory phase. The (average) frequency of these gaps can be controlled. However increasing the gap frequency reduces the required repetition-rate TR.

The TVI I(r,t) can be efficiently reconstructed from the TS-sampled data by interpolating the acquired data and performing one of the conventional reconstruction procedures on data corresponding to each time instant. In one preferred embodiment, the interpolation can be performed efficiently with a multi-dimensional linear shift-invariant filter that approximates a unit magnitude response over the DKT support.

The adaptive acquisition design method can be modified to find an MR acquisition scheme that satisfies additional constraints (for example, a limit on the maximum permissible repetition time for the pulse sequence) or fulfills other optimality conditions (for example, maximizing SNR). The condition (P2) can also be modified, so that more than one line, curve, or plane in k-space is acquired at one time.

RESPIRATORY MODEL: Respiratory motion is modeled by a time-varying affine transform of the spatial co-ordinates, i.e. the cardiac TVI with respiratory motion included is:

$$J(r,t) = I(P(t)r + q(t), t) \qquad \text{Eq. (2)}$$

where matrix $P(t) \in \mathbb{R}^{3 \times 3}$ and vector $q(t) \in \mathbb{R}^3$, define the affine motion at time t; and I(r,t) is the cardiac TVI in the absence of respiratory motion. This affine motion model subsumes other respiratory motion models like superior-inferior translation, lateral translation, 3D translation, rotation, expansion-contraction etc.

In practice, the motion in the imaged volume due to respiration may not be exactly affine. In that case, the model in Eq. (2) will represent the affine component of the respiratory motion and we will explicitly compensate for only this component of the motion. However, we note that the non-zero widths of the temporal bands in the banded spectral model for the cardiac TVI, will account for some of the residual non-affine motion and the overall imaging scheme will be robust to both affine and non-affine respiratory motion.

From Eq. (2) we derive the relation between the spatial Fourier transforms of I and J, to be:

$$I(k,t) = |P(t)|e^{-j2\pi k^T q(t)} J[P^T(t)k, t] \qquad \text{Eq. (3)}$$

where |P(t)| denotes the determinant of the matrix P(t) and superscript T denotes the transpose operation.

Qualitatively we can interpret the effect of affine motion of the object as having three distinct components:

I. Transformation of the k-space sample locations from k to $P^T(t)k$

II. Change in the phase of the k-space signal due to the translation of the object by q(t).

III. Change in the magnitude of the k-space signal by |P(t)| due to volumetric changes caused by the affine motion. (Note that the Jacobian |P(t)| represents the change in volume of a voxel due to the affine motion; in particular |P(t)|=1 implies that the volume of a voxel of the cardiac TVI does not change at time t) All these three effects need to be accounted for, in order to completely compensate for the effect of affine respiratory motion.

For an I(r,t) (the cardiac TVI in the absence of respiration) with DKT support $\beta_I$, we can reconstruct I from its samples at the k-space sample locations and sampling time-instants specified by the TS sampling schedule $\Psi^{TS}$. Thus in order to reconstruct I(r,t) we need a method to indirectly compute these sample values using MR data acquired while the subject is breathing. We next outline such a strategy.

ADAPTING TO RESPIRATORY MOTION: Conceptually, in a 3D MR experiment one measures the spatial-Fourier transform of the imaged object at a specified k-space sample location and a given time-instant. Hence the quantity J(k,t) can be experimentally measured for a free-breathing subject using an MR scanner and an appropriately designed pulse-sequence. Thus a prescriptive method for determining the desired quantity $I(k_0, t_0)$ (at a time-instant and k-space location specified by TS sampling schedule $\Psi$) is as follows:

A1. Adapt Sampling Schedule: At time $t_0$, measure $J(P^T(t_0)k_0, t_0)$ using an MR scanner.

A2. Phase Correction: Multiply the MR signal by the phase term $e^{-j2\pi k_0^T q(t_0)}$ either during acquisition (i.e. before signal demodulation) or later during reconstruction (i.e. after signal demodulation, A/D conversion etc).

A3. Jacobian Correction: Multiply the MR signal by the Jacobian correction term |P(t₀)| either during acquisition or later during reconstruction. This multiplication can be accomplished by various means, analog or digital, for eg., a variable gain amplifier or a digital multiplier.

Here it is assumed that we know the affine motion parameters $P(t_0)$ and $q(t_0)$ at the time-instant of interest. Later we will discuss how these quantities can be experimentally determined.

As described in (A1), the adaptation of the sampling schedule involves measuring data along the k-space trajectory determined by $P^T(t_0)k_0$, instead of along $k_0$ (which would be the k-space trajectory in the absence of respiratory motion) at time $t_0$. Noting that the k-space trajectory along which data is acquired in an MR experiment is determined by the set of gradients applied during the experiment (or more specifically by ∫G(t)dt, where G(t) is the gradient vector at time t), we propose a specific implementation of the sampling schedule adaptation, as follows:

A1'. Pulse Sequence Adaptation: Pre-multiply the gradients G(t) applied at time t by $P^T(t)$, i.e. apply gradients $P^T(t)$ G(t) instead.

When a slice-selective RF pulse is used in an MR experiment (either for 2D imaging to define an imaging slice, or in 3D imaging to define an imaging slab), the MR data depends upon both the k-space sample location and the selected slice. Prescription A is then modified as follows. The selected slice can be defined in terms of the spatial-selection function $\Psi(\mu^T r - \mu_0)$ that is specified by the triplet (B, μ, μ₀); B(·) (determined by the shape of the applied RF pulse) controls the slice-shape, μ affects the slice orientation and thickness, and μ₀ is the slice offset. Denote, for the TVI J(r,t), the MR data, corresponding to slice specified by (B, μ, μ₀) and sample location $k_0$, at time $t_0$ by $J_\mu^B(k_0, t_0; \mu_0)$. Then we derive:

$$I_\mu^B(k_0, t_0; \mu_0) = |P(t_0)| e^{-j2\pi k_o^T q(t_0)} J_{P^T(t_0)\mu}^B[P^T(t_0)k_0, t_0; \mu_0 + \mu^T q(t_0)]$$
Eq. (4)

From Eq. (4) we arrive at the following prescription for computing the desired quantity $I_\mu^B(k_0,t_0;\mu_0)$ for the specified slice and k-space sample location and sampling time instant defined by the TS sampling schedule Ψ:

B1. Adapt Sampling Schedule: At time $t_0$, measure $$J_{P^T(t_0)\mu}^B[P^T(t_0)k_0, t_0; \mu_0 + \mu^T q(t_0)]$$

using an MR scanner to sample k-space location $P^T(t_0)k_0$, for the slice (B, $P^T(t_0)\mu$, $\mu_0 + \mu^T q(t_0)$)

B2. Phase Correction: Multiply the MR signal by the phase term $e^{-j2\pi k_0^T q(t_0)}$ either during acquisition or later during reconstruction.

B3. Jacobian Correction: Multiply the MR signal by the Jacobian correction term |P(t₀)| either during acquisition or later during reconstruction.

As in the 3D case, a specific implementation of the sampling schedule adaptation involves modifying the gradients applied by the MR pulse sequence. Furthermore, since for the slice-selective MR experiment, we also need to adapt the slice for which data is acquired, we also modify the phase of the RF pulse (along with the gradients applied during slice selection). This leads to the following implementation of the sampling schedule adaptation:

B1'. Pulse Sequence Adaptation: Pre-multiply the pulse sequence gradients at time t by $P^T(t)$; and modulate the RF pulse at time t by $e^{j\mu^T q(t_0)t}$ For a 3D MR imaging experiment a TS sampling schedule $\Psi^{TS} = \{k^{TS}(n), nT_R\}$ is defined by the set of k-space locations $k^{TS}(n)$ sampled at the time instant $nT_R$. We define an Affine Corrected TS (ACTS) sampling schedule:

$$\Gamma = \{P^T(nT_R)k^{TS}(n), nT_R\}_n$$
Eq. (5)

to be the sampling schedule obtained by adapting the TS sampling schedule $\Psi^{TS}$ to the respiratory motion as prescribed in (A1).

For an MR imaging experiment in which slice-selective RF pulses are used, the TS sampling schedule also includes information about the slice that is excited at each acquisition time-instant. Hence in this case the TS sampling schedule $\Psi^{TS} = \{(B(n), \mu(n), \mu_0(n)), k^{TS}(n), nT_R\}_n$ is defined by: (1) the sampling time-instants $nT_R$; (2) the slice selected at time instant $nT_R$, specified by (B(n), μ(n), μ₀(n)); and (3) the set of k-space locations $k^{TS}(n)$ sampled at the time instant $nT_R$. Analogously to the above, we define an ACTS sampling schedule:

$$\Gamma = \{(B(n), P^T(nT_R)\mu(n), \mu_0(n) + \mu^T(n)q(nT_R)), P^T(nT_R)k^{TS}(n), nT_R\}_n$$
Eq. (6)

to be the adaptation of the TS sampling schedule to the respiratory motion according to prescription (B1).

DETERMINING RESPIRATORY MOTION PARAMETERS

The nine elements of the matrix P(t) and the three components of the vector q(t) must be known or estimated at the required sampling time-instants in order to determine the ACTS sampling schedule defined above. Assuming that the elements of the matrix P(t) are linearly independent of one another, up to 12 motion parameters would have to be measured for this purpose. However, this measurement can be significantly simplified by assuming that the object moves or expands only in one direction, for example, in the longitudinal direction of the subject. If this longitudinal direction corresponds to the z-axis, the vector q(t) is then simplified as:

$$q(t) = \begin{pmatrix} 0 \\ 0 \\ q_3(t) \end{pmatrix}$$
Eq. (7)

and the matrix P(t) then becomes $$P(t) = \begin{pmatrix} 1 & 0 & 0 \\ 0 & 1 & 0 \\ 0 & 0 & P_{33}(t) \end{pmatrix}$$
Eq. (8)

For this simplified motion model it is merely necessary to measure two motion parameters, for example the shift in position ($d_1$ and $d_2$) of two landmark points located on the heart during a respiratory cycle. The parameters $P_{33}(t)$ and $q_3(t)$ are then obtained as:

$$P_{33}(t) = \frac{d_1(t) - d_2(t)}{d_{1o} - d_{2o}}$$
Eq. (9)

$$q_3(t) = d_1(t) - \frac{d_1(t) - d_2(t)}{d_{1o} - d_{2o}} \qquad \text{Eq. (10)}$$

wherein, $d_{1o}$ and $d_{2o}$ represent the values of $d_1$ and $d_2$ at a diaphragm reference point that can be selected at random, for example, at the end of exhalation.

We can further reduce the measurement requirement (during the imaging scan) to the measurement of a single parameter, by introducing a prescan calibration step. During this calibration step, the values of $d_1$ and $d_2$ are correlated to the shift in position ($d_0$) of the diaphragm during the recurrent respiratory cycle. A rule describing the relationship between $d_0$ and $d_1$, $d_2$ represented as a fitted equation, or lookup table is stored. Consequently, during the subsequent MR examination it is no longer necessary to measure the values $d_1$ and $d_2$, but merely the quantity $d_0$, that is, the motion of the diaphragm. The associated values of $d_1$ and $d_2$ are then obtained directly from the stored values.

During the subsequent MR examination only the parameter $d_0$ need be measured, that is, in addition to the imaging MR signals. The values $P_{33}(t)$ and $q_3(t)$ can then be determined using the $d_1$ and $d_2$ values stored in the table in accordance with Eq. (9), Eq. (10) and the matrix P(t) and the vector q(t) can be derived therefrom in accordance with Eq. (7) and Eq. (8). These calculated affine motion parameters are then used to adapt the MR acquisition using either—prescription (A1)-(A3) or (B1)-(B3).

In general, when all 12 affine motion parameters, (or any subset thereof) are needed to model the respiratory motion accurately we derive a functional relationship between the required parameters and an easily observable or measurable quantity such as the diaphragm position parameter $d_0$ during a -prescan calibration of the respiratory motion. Then during subsequent MR examination, only the parameter $d_0$ needs to be measured and the required matrix P(t) and the vector q(t) can be derived. Alternatively, we measure the relevant affine motion parameters directly during the MR examination using MR navigators or auxiliary measurements.

Instead of using the diaphragm displacement alone, we can correlate the affine motion parameters to the signed diaphragm displacement wherein the displacement is assigned (say) a positive sign during inspiration and a negative sign during expiration. By observing whether the diaphragm displacement is increasing or decreasing relative to the previous measurement(s) one can determine whether the subject is inhaling or expiration. The advantage of using the signed $d_0$, is that it can overcome the hysteretic effect observed in the article titled "Free-breathing cardiac MR imaging: Study of implications of respiratory motion—Initial Results", by K. Nehrke et al., Radiology, 220:810-815 (2001). Respiratory bellows can be used as a substitute for, or to complement the measurement of $d_0$. Formally we refer to the parameter (or set of parameters) to which the affine motion parameters are correlated as the respiratory phase and denote it by $\eta$.

One aspect of the present invention is the recognition that the function that relates the affine-motion parameters to diaphragm motion ($d_0$) (or respiratory phase $\eta$ in general) may be different at different phases of the cardiac cycle. As a result, the above-described measurements and the resulting pulse-sequence adaptation may have to be produced separately for every cardiac phase at which images are going to be acquired.

During prescan one can also monitor temporal variation of $\eta(t)$ or its spectral content (energy in the temporal Fourier transform of $\eta(t)$) and use this knowledge to determine how often the respiratory phase will need to be measured during imaging. In particular if the spectrum of $\eta(t)$ has negligible energy in frequencies above $\hat{f}$ Hz;, it suffices to measure $\eta(t)$ at intervals not much smaller than $\frac{1}{2}\hat{f}$ seconds during imaging data acquisition. The values of $\eta(t)$ at other times can then be determined by extrapolation from known values for prospective compensation, or by interpolation for retrospective compensation.

RETROSPECTIVE RESPIRATORY MOTION CORRECTION: The respiratory motion compensation schemes (A1)-(A3) and (B1)-(B3) are prospective schemes, since they adapt the data to be acquired to the observed respiratory motion. However we can also (partially or wholly) compensate for respiratory motion retrospectively as described below.

In a 3D MR imaging experiment, we acquire data according to the TS sampling schedule (instead of the ACTS schedule) i.e. we skip the prescribed steps (A1) (or A1'). Then, the acquired data corresponds to $\{J(k,t)\}_\Psi$ i.e. samples of the cardiac TVI (with respiratory motion) at sample points determined by the TS sampling schedule, $\Psi$. Using Eq. (3) we then derive:

$$I(P^{-T}(t)k,t) = |P(t)|e^{-j2\pi k^T q(t)} J(k,t) \qquad \text{Eq. (11)}$$

Hence by applying prescribed steps (A2) and (A3) we can obtain samples of the cardiac TVI (without respiratory motion) I(k,t) at sample points determined by the following sampling schedule:

$$\Lambda = \{P^{-T}(nT_R)k^{TS}(n), nT_R\}_n \qquad \text{Eq. (12)}$$

From these samples, which are in general non-uniformly spaced in k-space, we need to reconstruct the cardiac TVI I(r,t) given that its DKT support is defined by $\beta_I$. This is a classical problem of bandlimited reconstruction from non-uniform samples, and can be solved using various known methods, including those described in the paper "Efficient numerical methods in non-uniform sampling theory" by Feichtinger, H. G., Grochenig, K., and Strohmer, T., published in Numerische Mathematik, v 69, n 4, 1995, p 423-40. Here we describe one approach. Let $\Omega$ be the set of all functions I(r, t) that are (i) consistent with the data, (ii) have the correct DKT support in (r,f) domain, and (iii) have energy bounded by some finite constant E; then we choose the reconstruction $\hat{I}(r,t)$ to be the one minimizing the worst case reconstruction error;

$$\hat{I}(r, t) = \underset{I \in \Omega}{\operatorname{argmin}} \underset{H \in \Omega}{\operatorname{sup}} \|I(r, t) - H(r, t)\| \qquad \text{Eq. (13)}$$

The solution to this problem is found using the Yen interpolator described by N. P. Willis and Y. Bresler, "Norm invariance of minimax-optimal interpolation," IEEE Trans. on Information Theory, vol. 38, no. 3, pp. 1177-1181, 1992. From this J(r,t) can be estimated, if desired, by using Eq. (2).

For retrospective respiratory motion correction, it is not necessary that the respiratory motion be modeled by an affine motion model as in Eq. (2). For instance, the effect of respiratory motion may be modeled as follows:

$$J(r,t) = I(p(r,t),t) \qquad \text{Eq. (14)}$$

where, J(r,t) and I(r,t) represent the imaged object with and without respiratory motion respectively; and p(r,t) is the motion field that defines how different points of the object move due to the subject's respiration. For such a respiratory motion model, the data collected by the MR scanner can be related to the TVI by the following relation:

$$J(k, t) = \int J(r, t)e^{-j2\pi k^T r} dr \qquad \text{Eq. (15)}$$

$$= \int I(p(r, t), t)e^{-j2\pi k^T r} dr$$

Note that, if the motion field p(r,t) is known, Eq. (15) represents a linear relationship between the desired TVI I(r,t). Using the MR scanner we can acquire samples of J(k,t) according to the TS sampling schedule. The problem of reconstructing the TVI I(r,t) from samples of J(k,t) is an example of classical inverse problem and methods for reconstruction are discussed in several texts, for instance, "Introduction to Inverse Problems in Imaging", by M. Bertero and P. Boccacci, IOP Publishing Ltd., 1998.

We now describe a specific approach to solving this problem analogous to the retrospective respiratory motion correction method used for the affine motion model case. Let $\Omega$ be the set of all functions I(r, t) that are (i) consistent with the data (i.e. Eq. (15)), (ii) have the correct DKT support in (r,f) domain, and (iii) have energy bounded by some finite constant E; then we choose the reconstruction $\hat{I}(r,t)$ to be the one minimizing the worst case reconstruction error;

$$\hat{I}(r, t) = \underset{I \in \Omega}{\operatorname{argmin}} \underset{U \in \Omega}{\sup} \|I(r, t) - U(r, t)\| \qquad \text{Eq. (16)}$$

As described above, the solution to this problem is found using the Yen interpolator.

The above description assumes that the respiratory motion field, p(r,t), is known or has been previously estimated. As in the affine respiratory motion model case, this motion field can be estimated based on a prescan model calibration step and respiratory navigator acquisition during the subsequent MR examination. In this case, instead of the affine motion parameters, we correlate the motion field p(r,t) with the respiratory phase $\eta(t)$, (for instance, the signed diaphragm displacement) during prescan. Then during imaging we estimate the respiratory phase using, for example, MR navigator data and hence obtain an estimate of the respiratory motion field at the time-instants of interest.

Alternatively, the cardiac TVI and motion field can be estimated jointly from the acquired MR data; for instance as a solution to the following optimization problem:

$$[I^*, p^*] = \qquad \text{Eq. (17)}$$

$$\underset{\substack{[\hat{I}, \hat{p}] \\ \operatorname{supp}[\hat{I}(r,f)] = \beta_I}}{\operatorname{argmin}} \left\{ \sum_{(k,t) \in \Psi} \left| J(k, t) - \int \hat{I}(\hat{p}(r, t), t)e^{-j2\pi k^T r} dr \right| + \delta(\hat{p}) \right\}$$

where $\Psi$ is the sampling schedule; J(k,t) is the acquired MR data; and $\delta(p)$ is a cost function penalizing deviation of the motion field from our a priori expectation. The optimization problem in Eq. (17) can be solved using general non-linear optimization techniques, for example discussed in "Nonlinear Programming", by D. P. Bertsekas, Athena Scientific, 1999, and implemented in numerical mathematical packages like Matlab. It is clear that the above formulation can be extended to incorporate parametric models of the motion field.

TIME-WARPED CARDIAC MODELS: The cardiac model based on the DKT support of the time-varying image can be modified and extended to derive other cardiac imaging schemes that too can be adapted to account for respiratory motion.

We present two methods that model the joint spatial and temporal-spectral characteristics of the beating heart. Furthermore we also explicitly model the aperiodicity of cardiac motion in the time-interval of interest by introducing a time-warp.

The time-varying image (TVI) models (in the absence of respiratory motion) we consider for cardiac applications can be expressed as:

$$I(r,t) = H(r; \phi(t)) \qquad \text{Eq. (18)}$$

where $\phi(t)$ represents the warping of the time-axis to account for the aperiodicity of the heart (for example due to heart rate variability); and H(r,t) represents an idealized chest cross-section. The function $\phi(t)$ is assumed to be monotonic in the time-interval of interest and to be approximately equal to t (note that for the case when $\phi(t)=t$ there is no time-warping). H(r,t) is zero outside the field of view (FOV) and H(k, t) has significant energy only for $\{k \in S\}$. This general model encompasses a wide variety of proposed cardiac imaging models but we focus on two models defined by a particular choice of the dual-k-t (DKT) support $\beta_H = \operatorname{supp}\{H(r, f)\}$ of the TVI.

Time-Warped Harmonic Model Adopting a temporally periodic model for the idealized cardiac TVI, each of its pixels is modeled as a sum of harmonically related complex sinusoids. The idealized cardiac TVI is thus expressed as:

$$H(r, t) = \sum_{m=-M}^{M} \alpha_m(r) e^{j2\pi m f_0 t} \qquad \text{Eq. (19)}$$

Figure 3:
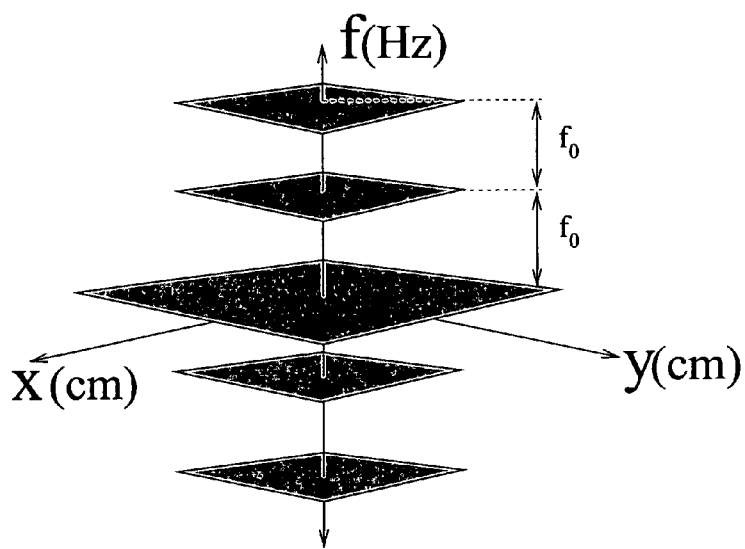
FIG. 3 is a graphic illustration of a dual k-t support for the time-varying image of a periodic beating heart.

However since the heart itself occupies only a fraction of the field of view, we expect only pixels corresponding to that portion of the image to have significant temporal variation and the rest of the image to be essentially static. This knowledge is incorporated in the model by imposing the constraint:

$$\alpha_m(r) = 0 \text{ if} \begin{cases} m = 0 \text{ and } r \in FOV \\ m \neq 0 \text{ and } r \in DFOV \end{cases} \qquad \text{Eq. (20)}$$

where the dynamic region of the image is limited to DFOV. The DKT support $\beta_H$ corresponding to this model is illustrated in FIG. 3. Note that though this model assumes that the idealized cardiac TVI H(r,t) is periodic in time, I(r, t) itself is in general aperiodic owing to the time-warp. (However, note that I(r, t) is a cyclic function of t, since for any fixed $r=r_0$ it is the composition of a periodic temporal function, $I(r_0, t)$, with a monotonic 'time-warp' function $\phi(t)$. Indeed the time-warp causes broadening of the line spectrum and $\beta_I = \operatorname{supp}[I(r, f)]$ to have a form similar to that in FIG. 4.

Figure 4:
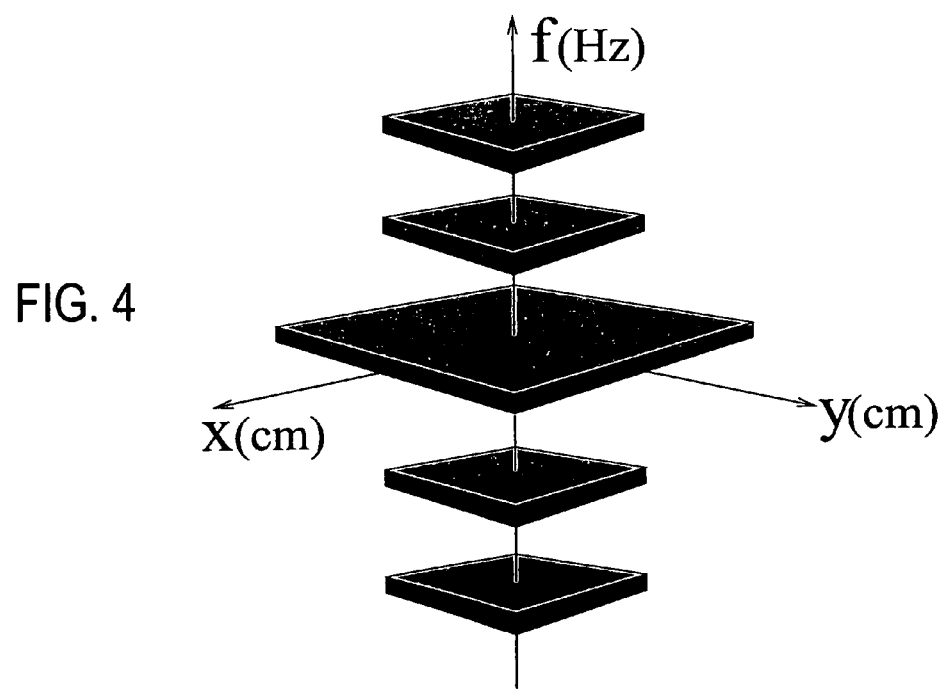
FIG. 4 is a graphic illustration of a dual k-t support for the time-varying image of an aperiodic beating heart.

Time-Warped Banded Spectral Model In this model, the idealized cardiac TVI, H(r, t) itself is assumed to have a banded $\beta_G$ of the form shown in FIG. 4 and the effect of the time-warp is simply to further broaden the temporal-spectral bands. The finite width of the temporal-spectral bands is introduced to account for any residual aperiodicity which may not be modeled by the time-warp (for example, if I(r, t) is not a perfectly cyclic function). Although this model is more general than the time-warped harmonic model, it also leads to more complicated reconstruction algorithm involving reconstruction of multi-band signals from non-uniform samples rather than a parameter estimation approach that can be used with the first model.

The effect of the time-warp $\phi(t)$ is to broaden the temporal spectrum of $I(r, t)$ when compared to $H(r, t)$. The average rate at which we need to sample a multi-dimensional function in order to reconstruct it without aliasing, depends on the occupied volume (area in the 2-D case) of its spectral support. One would thus expect that faster sampling is needed to reconstruct $I(r, t)$ than for reconstructing $H(r, t)$. However, we show how to estimate the time-warp $\phi(t)$ independently, and instead reconstruct $H(r, t)$ from its samples (acquired at a slower rate) and then use equation (10) to obtain $I(r, t)$. Thus, by modeling the cardiac aperiodicity explicitly we reduce the required k-space sampling rate during the scan.

As for the banded spectral cardiac model, we design the Time-Sequential sampling schedule for time-warped cardiac models based on the measured DKT support. However instead of the (broadened) DKT support of the time-warped function $I(r, t)$, we base the design on the narrower DKT support for the idealized cardiac function $H(r, t)$ in order to design the TS sampling schedule $\Psi$.

During imaging data acquisition we acquire data as determined by the previously designed TS sampling schedule $\Psi$, that determines the sequence and time-instants at which k-space is sampled. Since we also need to estimate the time-warp $\phi(t)$ during this imaging stage, we simultaneously acquire time-warp navigator data by sampling the center of k-space at $k_y=0$. This can be done, for example, by repeating the imaging pulse sequence without phase encoding or by using a single image pulse sequence that acquires two NMR echo signals per excitation, with the first echo used for acquiring imaging data and the second echo for acquiring reference data. The time-warp navigator data is dewarped to obtain the estimate of $\phi(t)$ during the imaging stage. The idea of dewarping is that given a cyclic function, we can dewarp each of its periods to obtain the underlying periodic function and estimate the time-warp. The dewarping operation is done efficiently using dynamic programming based algorithms. One such algorithm was described in "Dynamic Programming algorithm optimization of spoken word recognition" by H. Sakoe and S. Chiba in IEEE Transactions on Acoustics, Speech and Signal Processing, 26:43-49, 1978. Instead of MR reference data one can use data from other sources such as ECG to obtain this $\phi(t)$ estimate.

An alternative approach to estimating the time-warp function $\phi(t)$, is to use a parametric model, for instance:

$$\varphi(t) = t + \sum_{n=1}^{N} b_n \varphi_n(t) \quad t \in [0, T] \quad \text{Eq. (21)}$$

where, $\phi_n(t)$ are the known expansion functions and; $[0,T]$ is the time-interval of interest and $b_n$ are the unknown time-warp expansion coefficients. Possible choices of the expansion functions include the ones for polynomial time-warp model in which, $\phi_n(t)=t^{n+1}$, as described in, "Dynamic Magnetic Resonance Imaging based on optimal sampling and time-varying harmonic model", by Q. Zhao, N. Aggarwal and Y. Bresler, in Proc. ISMRM, 10, 2002. For an idealized cardiac TVI $H(r, t)$ that is (approximately) temporally-periodic, the MR data can be related to time-warp model as follows:

$$I(k, t) = \sum_{m=-M}^{M} \alpha_m(k) e^{j2\pi m f_0 \varphi(t)} + \varepsilon(k, t) \quad \text{Eq. (22)}$$

$$= \sum_{m=-M}^{M} \alpha_m(k) e^{j2\pi m f_0 [t + \sum_{n=1}^{N} b_n \varphi_n(t)]} + \varepsilon(k, t)$$

where $\epsilon(k,t)$ is the residual function that accounts for modeling errors and noise. Using Eq. (22), we can estimate the unknown quantities using, for instance, the least-squares approach, i.e.:

$$\{\alpha_m(k), b_n, f_0\} = \quad \text{Eq. (23)}$$

$$\operatorname*{argmin}_{\{\alpha_m(k), b_n, f_0\}} \sum_{(k,t) \in \Psi} \left| I(k, t) - \sum_{m=-M}^{M} \alpha_m(k) e^{j2\pi m f_0 [t + \sum_{n=1}^{N} b_n \varphi_n(t)]} \right|^2$$

where, $\Psi$ represents the points in (k,t) space for which MR data is acquired. From this estimate of the time-warp expansion coefficients, the time-warp can itself be estimated using Eq. (21). Again, it should be clear, that instead of MR reference data one can use data from other sources such as ECG to obtain this $\phi(t)$ estimate.

Reconstruction for Time-Warped Harmonic Model To reconstruct the object $I(r, t)$ we need to estimate the model parameters $f_0$ and $\{\alpha_m(r)\}$. First, the fundamental temporal frequency $f_0$ is estimated from the dewarped MR time-warp navigators using nonlinear least-squares. Next, the $\{\alpha_m(r)\}$ are estimated using the acquired data $I(k^{TS}(n), nT_R)$ as follows. Combining Eq. (18) and Eq. (19) and taking the Fourier transform with respect to r we have:

$$I(k^{TS}(n), nTr) = \sum_{m=-M}^{M} \left( \int_R \alpha_m(r) e^{-j2\pi [k^{TS}(n)]^T r} dr \right) e^{j2\pi m f_0 \varphi(nTr)} \quad \text{Eq. (24)}$$

Because $I(r, t)$ is essentially band-limited in k, $\alpha(r)$ can be discretized on a rectangular grid. This relation along with the constraints of Eq. (20), yields an over-determined system of linear equations for the unknown $\alpha$'s (on the discretization grid), which we solve in the least-squares sense.

It should be apparent that if a parametric model is used to model the time-warp, then the time-warp expansion coefficients $\{b_n\}$, and the TVI model parameters $f_0$ and $\{\alpha_m(r)\}$ can be estimated jointly, using Eq. (21) and Eq. (24).

Reconstruction for Time-Warped Spectral Band Model From (13)Eq. (18) it is seen that the acquired data $I(k^{TS}(n), nT_R)$ corresponds to samples of $H(k, t)$ non-uniformly spaced in (warped) time. However we know that the spectrum of H (in (r,f)) has support $\beta_H$, and we need to estimate the values of $H(r,t)$ for arbitrary r and t from this knowledge. This is again a classical problem of bandlimited reconstruction from non-uniform samples, similar to the problem described in context of Retrospective Respiratory Compensation, and can be solved using various known methods, including those described in the paper "Efficient numerical methods in non-uniform sampling theory" by Feichtinger, H. G.; Grochenig, K.; and Strohmer, T., published in Numerische Mathematik, v 69, n 4, 1995, p 423-40. Here we describe one approach. Let $\Omega$ be the set of all functions $H(r, t)$ that are (i) consistent with the data, (ii) have the correct support in (r,f), and (iii) have energy bounded by some finite constant E; then we choose the reconstruction $\hat{H}(r,t)$ to be the one minimizing the worst case reconstruction error;

$$\hat{H}(r, t) = \underset{H \in \Omega}{\arg\min} \underset{U \in \Omega}{\sup} \|H(r, t) - U(r, t)\| \qquad \text{Eq. (25)}$$

The solution to this problem is found using the Yen interpolator and, if desired, I(r,t) can be recovered using Eq. (18).

Adapting to Respiratory Motion As in Eq. (2) we again model the effect of respiratory motion on the cardiac TVI by the time-varying affine motion model J(r,t)=I(P(t)r+q(t),t). However now the respiration-free cardiac TVI is modeled by either the Time-Warped Harmonic Model Eq. (19) and Eq. (20) or the Time-Warped banded spectral model.

In either case, in order to reconstruct I(r, t), we need to measure the values of I(k, t) at k-space sample locations and sampling instants determined by the TS sampling schedule $\Psi$. We also need to measure the time-warp navigator data which corresponds to samples of I(k, t) along the $k_y=0$ line in k-space for time instants that are integer multiples of $T_R$.

We use the same adaptation strategy prescribed in (A1)-(A3), (A1',A2,A3), (B1)-(B3) or (B1',B2,B3) described earlier in order to obtain these sample values. However, we now apply the adaptations to acquisition of both the imaging and time-warp reference data. Following the adaptation of the acquisition to the observed respiratory motion, the cardiac TVIs can be reconstructed using either Eq. (24) or Eq. (25).

DESCRIPTION OF THE PREFERRED EMBODIMENT

For the preferred embodiment we describe the application of our method to imaging of a 2D cardiac slice using a spin-warp pulse-sequence. For notational convenience, x, y and z are chosen to be the desired readout, phase-encoding and slice-select directions respectively. Embodiments for other imaging scenarios, like 3D imaging or projection imaging (radial sampling in k-space) can be analogously derived based on the general description given in the previous section.

MR IMAGING SYSTEM Referring first to FIG. 1, there is shown the major components of a preferred MRI system that incorporates the present invention. The operation of the system is controlled from an operator console 100, which includes a keyboard and control panel 102 and a display 104. The console 100 communicates through a link 116 with a separate computer system 107 that enables an operator to control the production and display of images on the screen 104. The computer system 107 includes a number of modules that communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121, which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data that indicates the timing, strength and shape of the RF pulses that are to be produced, and the timing of and length of the data acquisition window. The pulse generator module 121 connects to a set of gradient amplifiers 127, to indicate the timing and shape of the gradient pulses to be produced during the scan. The pulse generator module 121 also receives subject data from a physiological acquisition controller 129 that receives signals from a number of different sensors connected to the subject, such as ECG signals from electrodes or respiratory signals from a bellows. And finally, the pulse generator module 121 connects to a scan room interface circuit 133, which receives signals from various sensors associated with the condition of the subject and the magnet system. It is also through the scan room interface circuit 133 that a subject positioning system 134 receives commands to move the subject to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141, which includes a polarizing magnet 140 and a whole-body RF coil 152. A transceiver module 150 in the system control 122 produces pulses, that are amplified by an RF amplifier 151 and coupled to the RF coil 152 by a transmit/receive switch 154. The resulting signals radiated by the excited nuclei in the subject may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF local coil to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to reconstruct the desired images using the acquired data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

Figure 2:
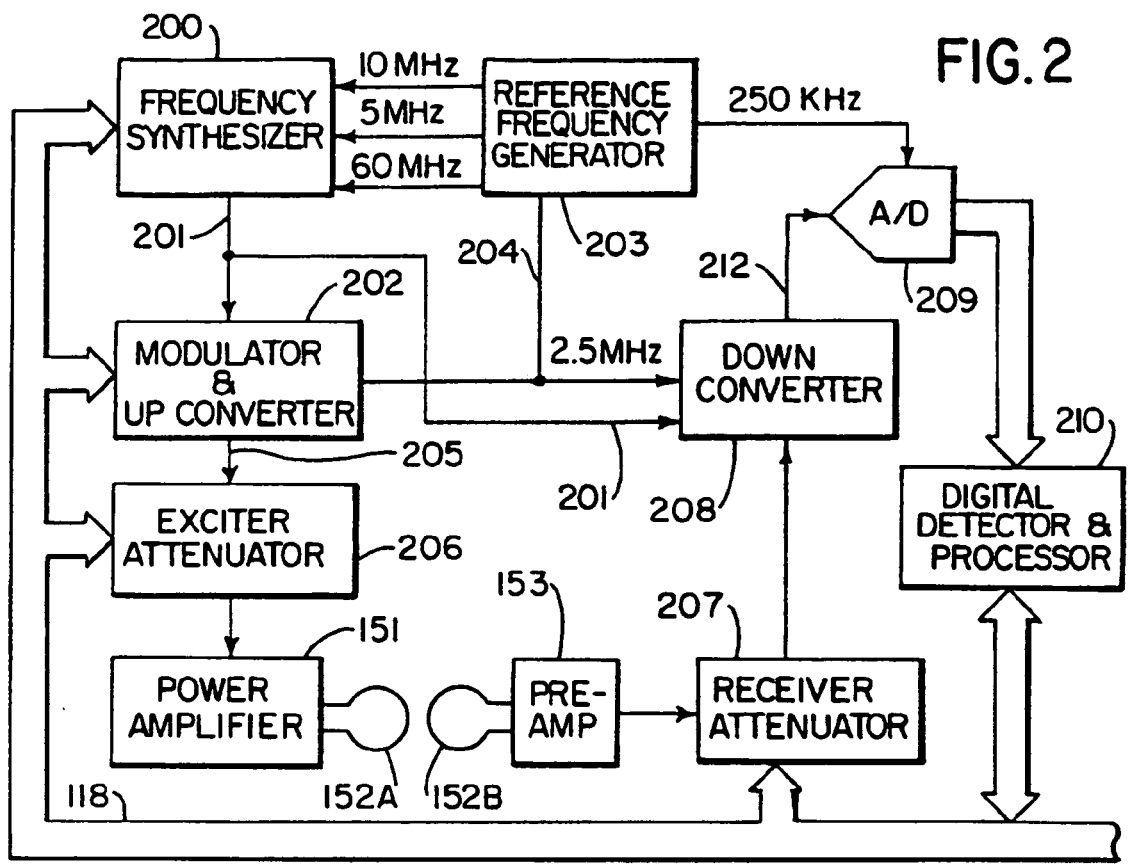
FIG. 2 is an electrical block diagram of the transceiver that forms part of the MRI system of FIG. 1.

Referring particularly to FIGS. 1 and 2, the transceiver 150 produces the RF excitation field B1 through power amplifier 151 at a coil 152A and receives the resulting signal induced in a coil 152B. As indicated above, the coils 152A and B may be separate as shown in FIG. 2, or they may be a single whole body coil as shown in FIG. 1. The base, or carrier, frequency of the RF excitation field is produced under control of a frequency synthesizer 200, which receives a set of digital signals from the CPU module 119 and pulse generator module 121. These digital signals indicate the frequency and phase of the RF carrier signal produced at an output 201. The commanded RF carrier is applied to a modulator and up converter 202 where its amplitude is modulated in response to a signal also received from the pulse generator module 121. This signal defines the envelope of the RF excitation pulse to be produced and is produced in the module 121 by sequentially reading out a series of stored digital values. These stored digital values may, in turn, be changed to enable any desired RF pulse envelope to be produced.

The magnitude of the RF excitation pulse produced at output 205 is attenuated by an exciter attenuator circuit 206, which receives a digital command from the backplane 118. The attenuated RF excitation pulses are applied to the power amplifier 151 that drives the RF coil 152A.

Referring still to FIGS. 1 and 2 the signal produced by the subject is picked up by the receiver coil 152B and applied through the preamplifier 153 to the input of a receiver attenuator 207. The receiver attenuator 207 further amplifies the signal by an amount determined by a digital attenuation signal received from the backplane 118. The received signal is at or around the Larmor frequency, and this high frequency signal is down converted by a down converter 208, which first mixes the NMR signal with the carrier signal on line 201 and then mixes the resulting difference signal with the 205 MHz reference signal on line 204. The down converted NMR signal is applied to the input of an analog-to-digital (A/D) converter 209, which samples and digitizes the analog signal and applies it to a digital detector and signal processor 210, which produces 16-bit in-phase (I) values and 16-bit quadrature (Q) values corresponding to the received signal. The resulting stream of digitized I and Q values of the received signal are output through backplane 118 to the memory module 160 where they are employed to reconstruct an image.

The 2.5 MHz reference signal as well as the 250 kHz sampling signal and the 5, 10 and 60 MHz reference signals are produced by a reference frequency generator 203 from a common 20 MHz master clock signal.

Figure 7:
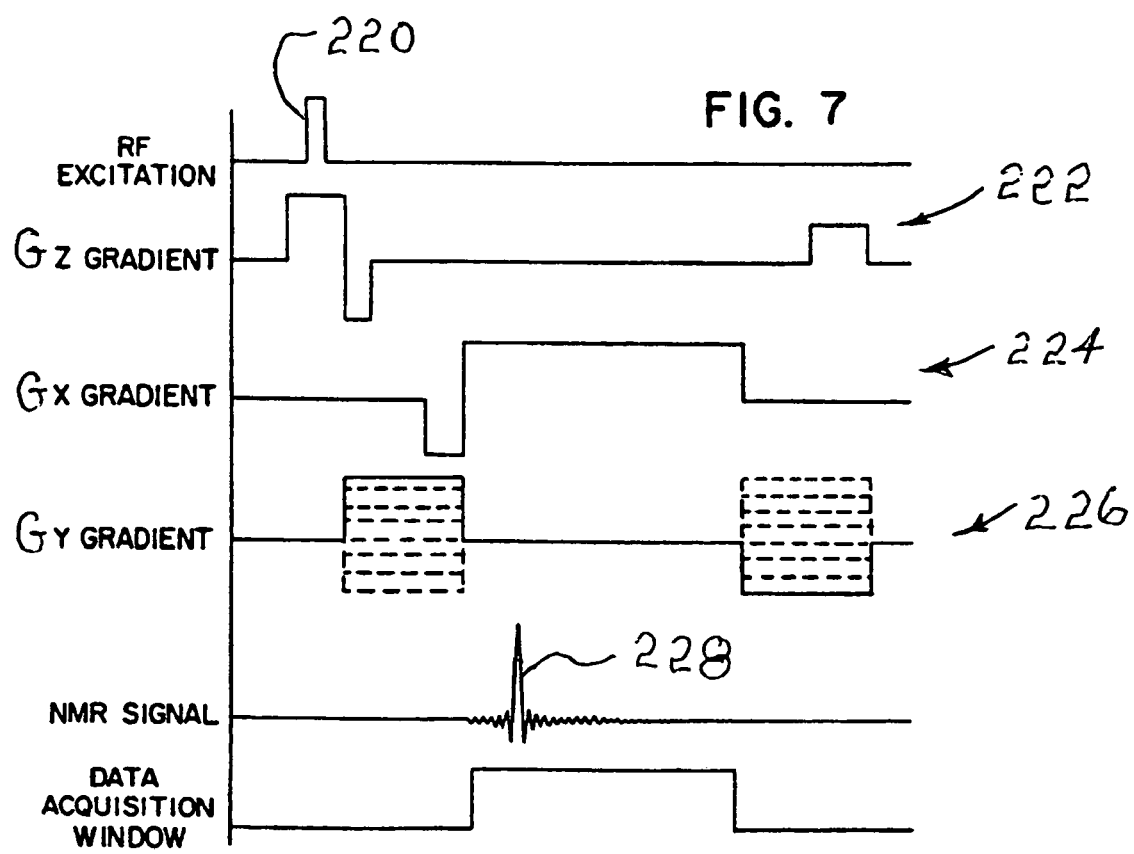
FIG. 7 is a graphic illustration of a preferred imaging pulse sequence used to practice the present invention.

Although a number of fast pulse sequences may be employed to practice the invention, in the preferred embodiment a spoiled gradient-recalled echo sequence or a steady-state gradient-recalled echo pulse sequence such as that shown in FIG. 7 is employed. The pulse sequence includes a selective rf excitation pulse 220 having a prescribed flip angle. The frequency and phase of this excitation pulse 220 can be precisely controlled by the MR scanner hardware as described above. The pulse sequence produces three gradient waveforms $G_z(t)$ 222, $G_x(t)$ 224 and $G_y(t)$ 226. $G_z(t)$ 222 is a slice select gradient, which operates in combination with the selective RF excitation pulse 220 to excite spins in a slice of prescribed thickness and location. $G_x(t)$ 224 is a readout gradient that frequency encodes the NMR signal 228 as it is acquired by the transceiver 150. And finally, $G_y(t)$ is a phase encoding gradient which phase encodes the NMR signal 228 to sample a particular $k_y$ line in k-space. This phase encoding gradient is set to a particular value during each pulse sequence and this value is changed each time the pulse sequence is repeated to sample a different $k_y$ line in k-space. One aspect of the present invention is the order in which the $k_y$ lines of k-space are acquired. As will be explained in more detail below, during a prescan a sampling schedule is produced, and the values in this table are used during the scan to set the phase encoding gradient value during each repeat of the pulse sequence such that the $k_y$ lines in k-space are acquired in the proper order and at the proper time. This sampling schedule is adapted to the respiratory motion of the subject being imaged. As a result, the k-space data acquired may correspond to an oblique slice in the lab frame, and k-space sample locations may not be parallel to the y-axis.

Figure 8:
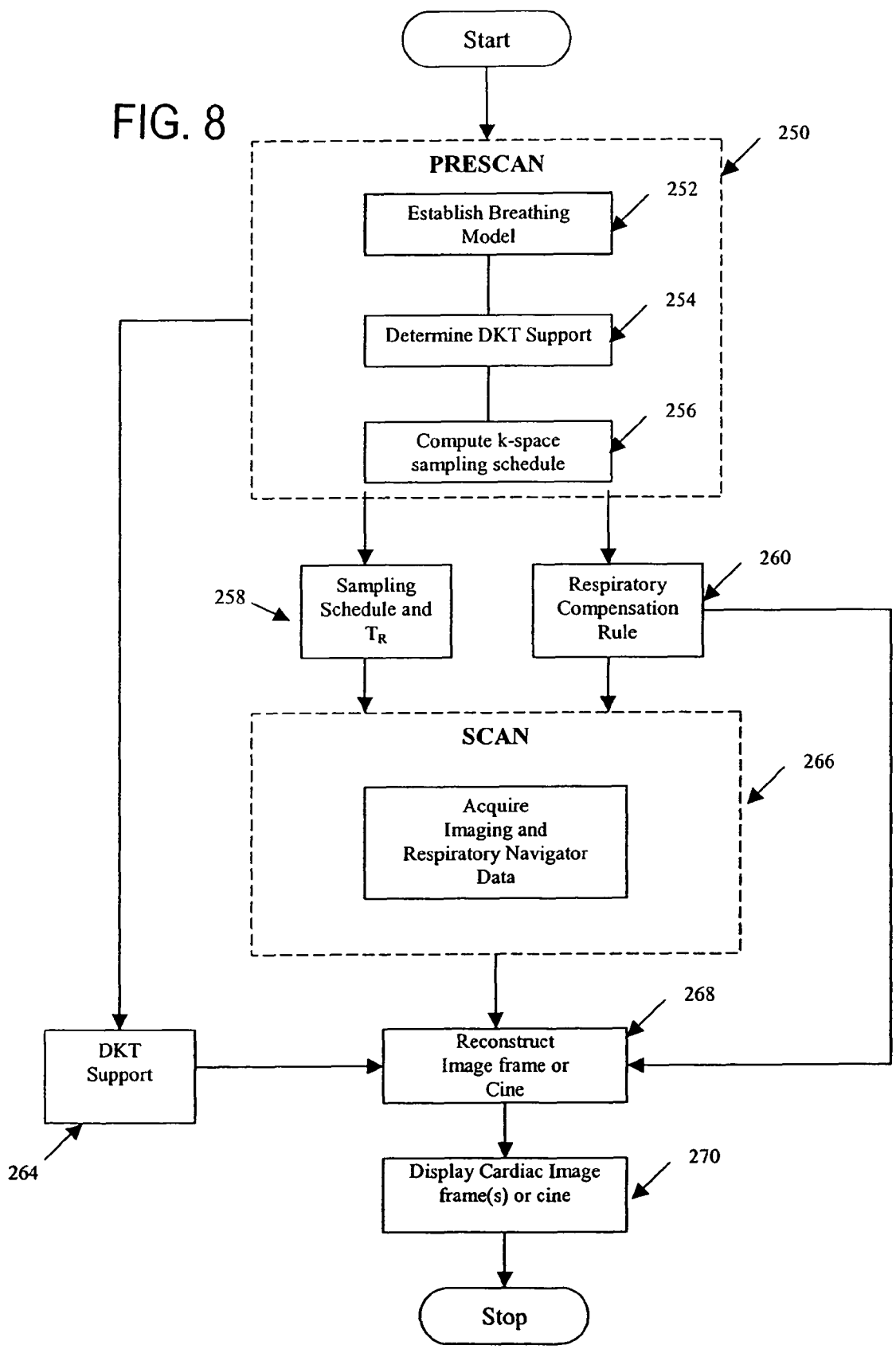
FIG. 8 is a flow chart of the steps in the preferred embodiment of the MRI scanning method of the present invention.

IMAGING SCHEME OVERVIEW Referring particularly to FIG. 8, the acquisition and display of cardiac images according to the present invention may be separated into four separate stages: (1) a prescan indicated at process block 250; (2) a scan indicated generally at 266, (3) an image reconstruction step indicated at 268 and, (4) an image display stage indicated at 270.

The prescan 250 itself consists of three stages. As will be explained in detail below, in stage 252, during the prescan 250 data is acquired from the subject of the examination, this data, relating diaphragm position ($d_O$) to respiratory motion in the imaged volume of interest. This is done at one or more cardiac phases and the resulting values are stored in a respiratory compensation table 260. During the prescan in stage 254 MR data is also acquired with the above-described imaging pulse sequence, but with the directions of the phase encoding gradient and readout gradient swapped. As will be described in more detail below, this data is employed in prescan stage 256 to produce an optimal sampling schedule 258 that adapts the MR data acquisition to the particular subject of this examination.

After the prescan 250 is completed, the imaging scan is then performed as indicated at process block 266 using the above-described imaging pulse sequence. The order and times in which $k_y$ lines of k-space are sampled is determined by the sampling schedule 258. Each acquisition prescribed by this sampling schedule is adapted to the respiratory motion of the subject using the respiratory compensation table 260 and a real-time measure of diaphragm position ($d_O$).

After the k-space data indicated by the sampling schedule 258 has been acquired, one or more images of the heart at the selected time-instant are reconstructed and displayed as indicated by process block 268 and 270 respectively. As will be explained in more detail below, this image reconstruction is more than the usual two-dimensional DFT or inverse DFT along the respective $k_x$ and $k_y$ axes, but it is still accomplished very quickly. The same data-set can be used to reconstruct the cardiac TVI at different time-instants corresponding to varying cardiac and respiratory phases.

PRESCAN Referring particularly to FIG. 8, the purpose of the prescan process 250 is to produce the respiratory compensation table 260, the sampling schedule 258 and an estimate of the DKT support 264, which are used during the MRI scan and image reconstruction stages. The respiratory compensation table 260 is produced first because, as explained below, it can be used to compensate for respiratory motion when acquiring data for Dynamic Model Estimation.

RESPIRATORY MODEL ESTIMATION The respiratory compensation table 260 in FIG. 8 may be produced for specific cardiac phases because the impact of respiratory motion on heart motion is different when the heart is at different phases of its cardiac cycle. The process is described in FIG. 9, with further elaboration in FIG. 10. The initial cardiac phase is input as indicated at process block 300 and the system waits at decision block 302 for the subject's heart to reach this phase as indicated by a ECG signal and shown in FIG. 10.

A navigator pulse sequence is then performed to acquire current diaphragm position as indicated at process block 304. This navigator pulse sequence is indicated at 305 in FIG. 10, and as is well known in the art, it is a pulse sequence in which the phase encoding gradient ($G_y$ in the preferred embodiment) is set to zero, and which generates a NMR signal that is Fourier transformed to produce a magnitude image from which the diaphragm position ($d_O$) is detected. Other navigator pulse sequences as described in "Orbital navigator echoes for motion measurements in magnetic resonance imaging" by Z. W. Fu et al, Magnetic Resonance in Medicine, 34, pp 746-753, 1995, may also be used for this estimation of respiratory motion.

Figure 10:
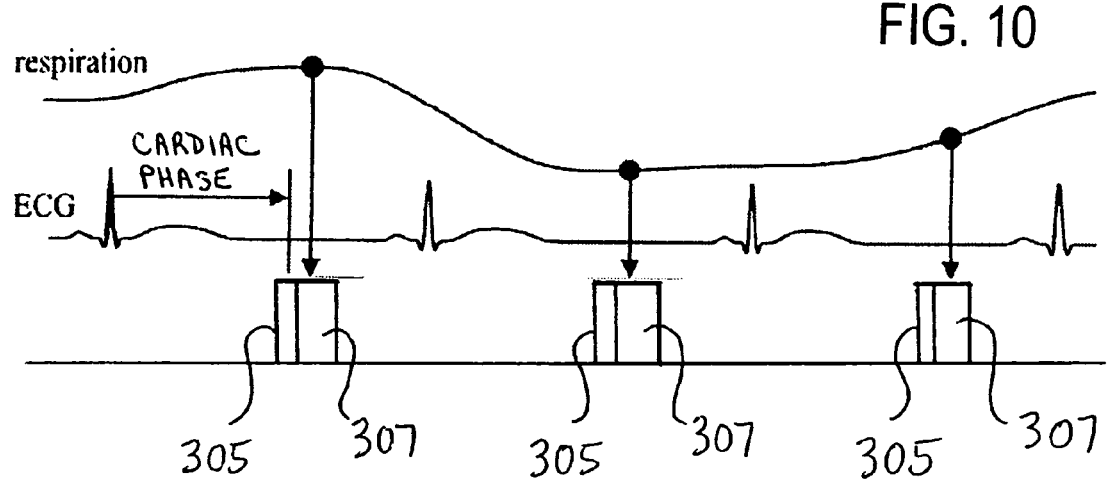
FIG. 10 is a graphic illustration of the synchronization of the data acquisition during the prescan stage shown in FIG. 9 with the subject's heart beat and respiration;.

The navigator acquisition is immediately followed by the acquisition of a low resolution, 3D image of the heart as indicated by process block 306. As shown in FIG. 10, this image acquisition 307 employs a multi-2-D fast gradient echo sequence consisting of two RF excitations per image slice (TR=7.1 ms, TE=2.6 ms, flip angle=45°/90°), each followed by nine echo planar imaging (EPI) readouts covering k-space in an interleaved fashion. The resulting k-space matrix of 32×18 (half-Fourier k-space coverage 0.6) is reconstructed to form an image matrix of 64×64 pixels to get a smoother image contrast, which is advantageous for the subsequent motion registration. A single slice can be acquired in less than 15 ms, which is short enough to freeze cardiac motion during the acquisition. Typically, eight slices are measured for each cardiac phase to obtain one complete 3-D data set. A field of view of 256×256 mm² and a slice thickness of 8 mm results in a reconstructed voxel size of 4×4×8 mm³ at an actual resolution of (8 mm)³. T2-preparation and a fat suppression pulse may be used prior to the imaging sequence to enhance image contrast.

Figure 9:
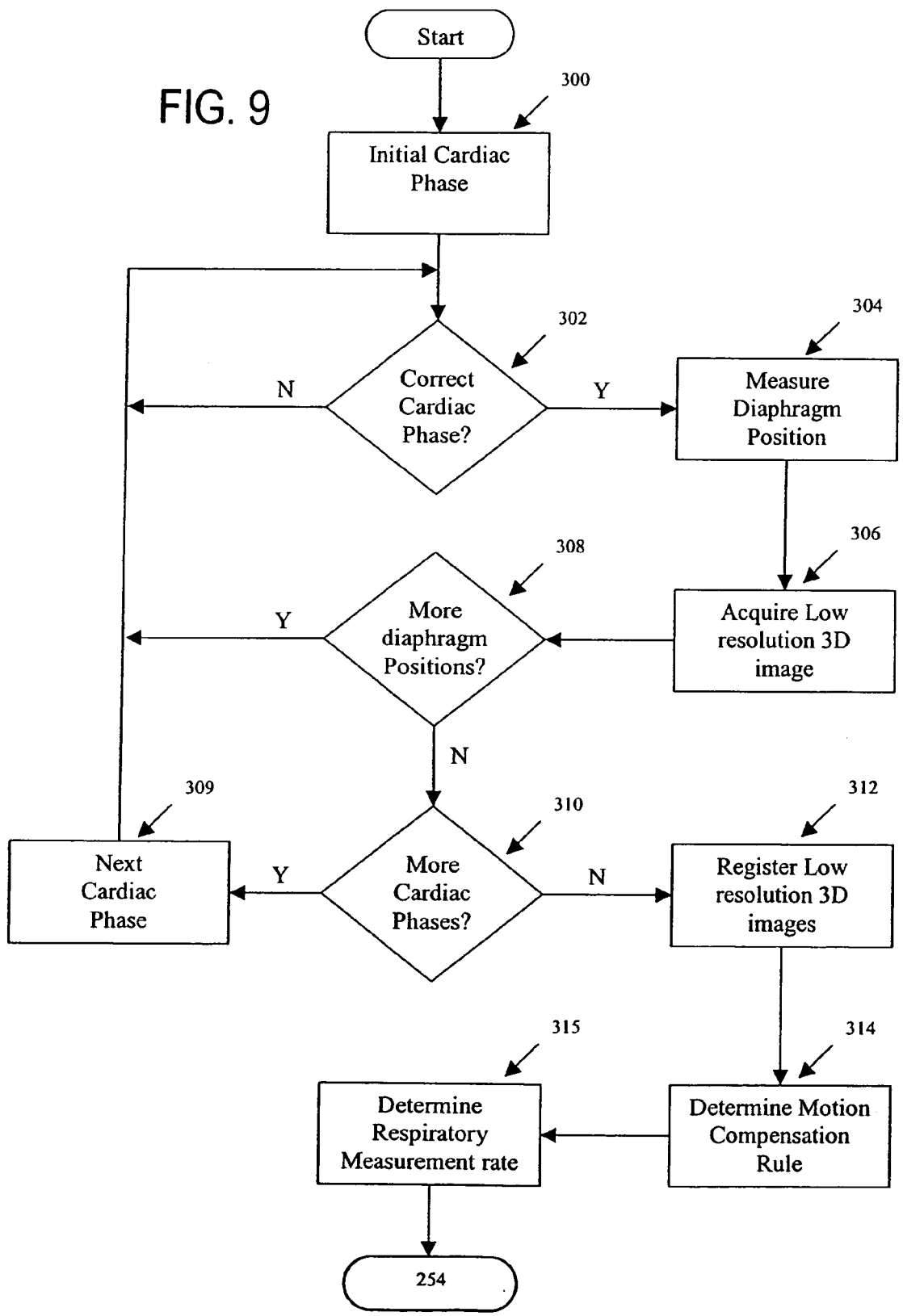
FIG. 9 is a flow chart of steps in a prescan stage of the scanning method of FIG. 8, which are used to establish the respiratory motion model.

The acquisition of low resolution 3D images of the heart and concurrent diaphragm position measurement continues until images are acquired over a suitable range of diaphragm positions as indicated in FIG. 9 at decision block 308. For greater accuracy, the respiratory motion calibration may be repeated for different cardiac phases, albeit at the cost of greater prescan time requirement. Thus, if desired, as determined at decision block 310, the system loops back and repeats the acquisition of additional sets of low resolution images at the prescribed cardiac phases.

Specific points, or landmarks, on the imaged heart can be located in the acquired images and used to model the motion caused by respiration as described above. However, in the preferred embodiment this motion information is derived using image-intensity-based registration as indicated at process block 312. For registration of the low-resolution 3D MR images, one of the MR images representing end-expiration is chosen as a reference.

The fast rigid and affine registration is based on a method which employs the standard cross-correlation or local correlation measure, which can be formulated as a least squares criterion. This enables the application of dedicated optimization methods, in particular Gauss-Newton optimization. Apart from its speed, Gauss-Newton optimization has the advantage that it can be extended to 3D affine transformations without loss of stability. The current task, namely, the registration of low-resolution 3D MR images, is a single modality problem. Thus, the cross-correlation measure is used. A detailed description of the registration algorithm is given in T. Netsch, P. Rosch, A. van Muiswinkel, and J. Weese, "Toward real-time multi-modality 3D medical image registration," in Proc. Int. Conf. Computer Vision ICCV, 2001, pp. 501-508. Many other registration methods are known in the art and, "A review of cardiac image registration methods" by T. Makela et al, IEEE Transactions on Medical Imaging, 21 (9): 1011-1021, 2002 reviews some of these methods.

The output of the registration step is a vector a(t) describing a rigid or affine transformation of each 3D image to transform the image to closely approximate the reference image. Each vector a(t) represents the detected motion of one 3D time frame acquired at the point of time t. In the case of the 3D translation model, $a(t)=[d_x, d_y, d_z]^T$ contains three translation components; in the case of the affine transformation, $a(t)=[a_{xx} \ldots a_{zz}, d_x, d_y, d_z]^T$ contains nine parameters representing a 3D linear transformation and additionally the three translation components of the current time frame. Besides the motion parameters a(t), the (signed) diaphragm position d0 was measured at the same times (t).

As indicated at process block 314 of FIG. 9, the next step is to calculate the relation between diaphragm motion $d_0(t)$ and the motion parameters a(t). A linear regression is applied to determine linear fits between each motion parameter and the diaphragmatic position. Hence, nonlinear effects are neglected in the motion analysis. The regression slopes determined for each motion parameter are stored in the respiration compensation table 260 of FIG. 8. Alternatively we can use a linear or non-linear, parametric or non-parametric model to estimate the relation between the respiratory motion parameters and the diaphragm motion and store the resultant model information in table 260.

As indicated at process block 315 of FIG. 9, after the compensation parameters are stored in the table 260 they are examined to calculate a respiration measurement rate, which is also stored in the table 260. The respiration measurement rate indicates how frequently the diaphragm position of the subject under examination needs to be measured in order to keep track of the subject's respiratory phase throughout the breathing cycle. It can be appreciated that for a subject with slow and regular inspiration-expiration, the diaphragm position needs to be measured less often. By establishing how quickly and smoothly the diaphragm position ($d_0$) varies, this rate can be determined. This rate can vary from 2 updates/second to 20 updates/second.

Alternatively the respiration measurement rate can depend upon the measured diaphragm position; and indicates at any measured diaphragm position ($d_0$) the amount of time that may elapse before the diaphragm position needs to be measured again. The reason for choosing a non-uniform respiration measurement rate is that during some portions of the respiratory cycle there is very little respiration-induced cardiac motion, whereas at other times the heart is moved significantly. By establishing a cardiac movement threshold and examining the measured motion parameters, the relation between diaphragm position ($d_0$) and the time-interval before the next respiratory navigator needs to be applied can be calculated.

Between consecutive measurements of the diaphragm position, the respiratory phase can be updated by extrapolating from the previously recorded phase history. Observation of the subject's respiration during pre-scan is used to establish a model of how a subject's respiratory phase varies with time. Model information is also stored in the respiratory compensation table and guides the respiratory phase extrapolation.

Referring particularly to FIG. 8, the remainder of the prescan process is employed to estimate the Dynamic Model $M(\alpha)$ and to design the sampling schedule $\Psi$ 256. For the preferred embodiment, we discuss in detail the case when the banded spectral model is used as the dynamic cardiac model. For this case we estimate the DKT support $\beta_I$ 254 during the prescan as will now be described.

DYNAMIC MODEL ESTIMATION Recall that the DKT support of the cardiac TVI (in the absence of respiratory motion) is defined as $\beta_I \Delta \text{supp}\{I(r,f)\}$ where r denotes a spatial variable and f is the temporal frequency. For 2D spin-warp imaging, during imaging data is acquired along k-space lines parallel to the (readout) $k_x$-axis. Since data along this readout direction is acquired almost instantaneously (i.e. cardiac motion during the readout time interval is negligible) and is sampled finely (w.r.t the Nyquist sampling rate determined by the field-of-view along the x-direction), we can ignore the effects of sampling along the $k_x$-dimension. Hence we can re-define the DKT support $\beta_I$ as follows:

$$\mathcal{B}_I = \bigcup_x supp\{I(x, y, f)\} \quad \text{Eq. (26)}$$

where $$\bigcup_x$$

denotes the union over all x in the FOV. The aim of the Dynamic Model Estimation is to estimate this DKT support $\beta_I$.

Figure 11A:
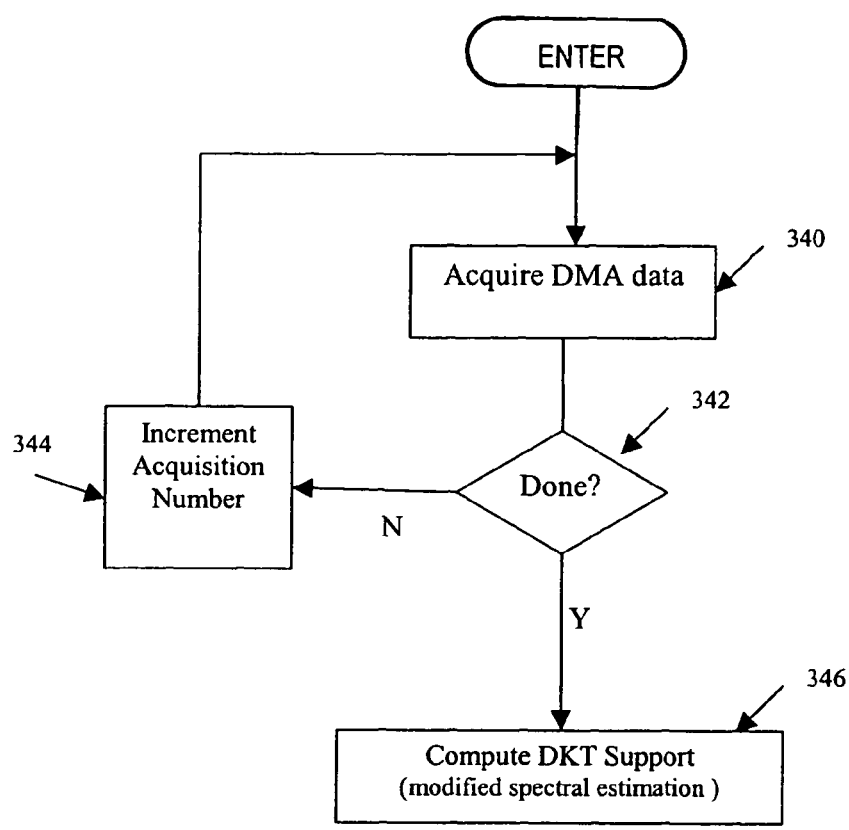
FIGS. 11A-11C are a set of flow charts of steps in a prescan stage of the scanning method of FIG. 8, in which each flow-chart outlines a different method for estimating the dual-k-t support for the imaged object.
Figure 11B:
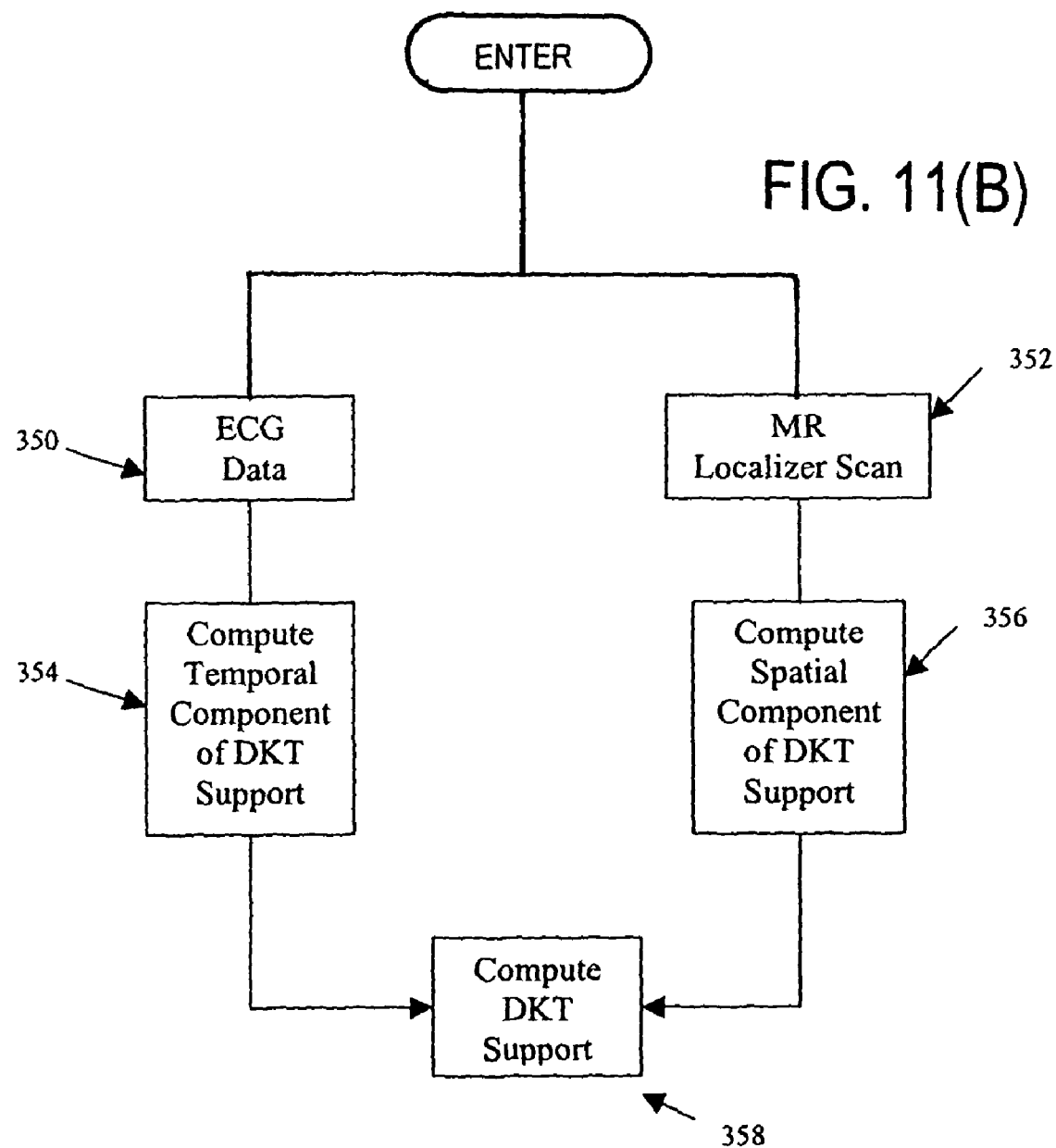
Figure 11C:
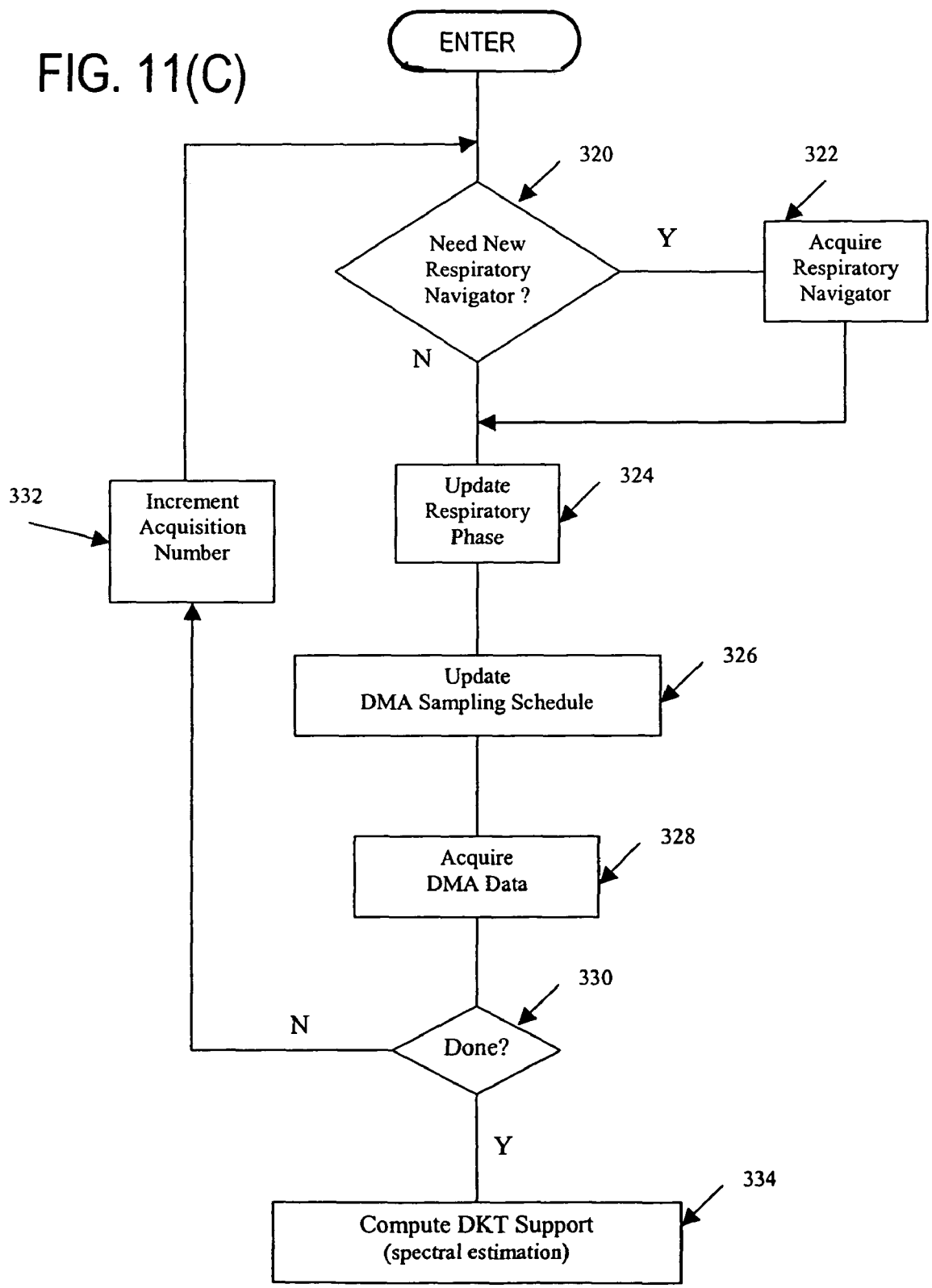

There are several alternative methods for measuring the DKT support of the TVI as illustrated in FIGS. 11(a)-(c). We begin by describing the method illustrated in FIG. 11(a). Note that the DKT support as defined by Eq. (26), can also be expressed as:

$$\mathcal{B}_I = \bigcup_{k_x} \underbrace{supp\{I(k_x, y, f)\}}_{\mathcal{B}_I(k_x)} \quad \text{Eq. (27)}$$

This indicates that we can estimate the marginal DKT support $\beta_I(k_x)$ for a sufficiently dense set of $k_x$-sample locations ($k_x^0$, $k_x^1$, ..., $k_x^N$) and then estimate the required DKT support by forming the union of these marginal supports.

Figure 5:
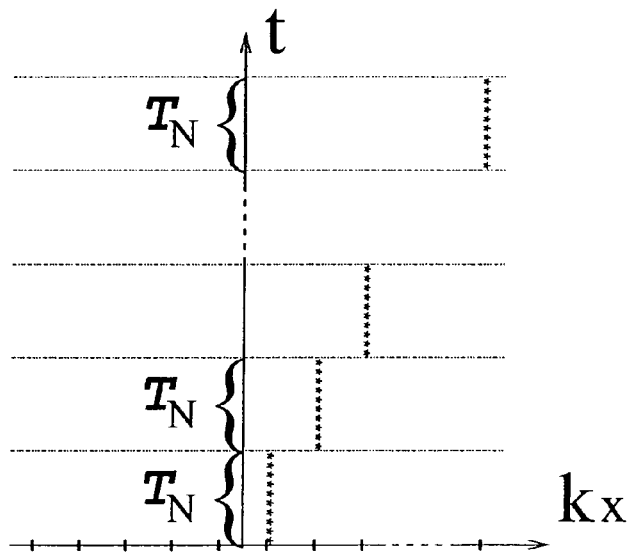
FIG. 5 is a graphic illustration of a k-space sampling schedule that may be employed during a prescan stage of the preferred method to estimate the DKT support for the imaged object.
Figure 6:
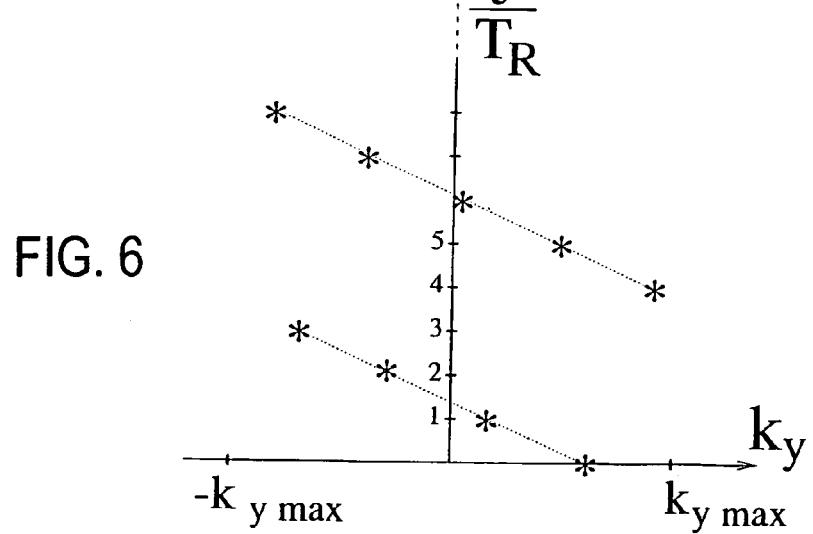
FIG. 6 is a graphic illustration of the resulting k-space sampling schedule that may be employed during the imaging phase of the preferred method.
Figure 12:
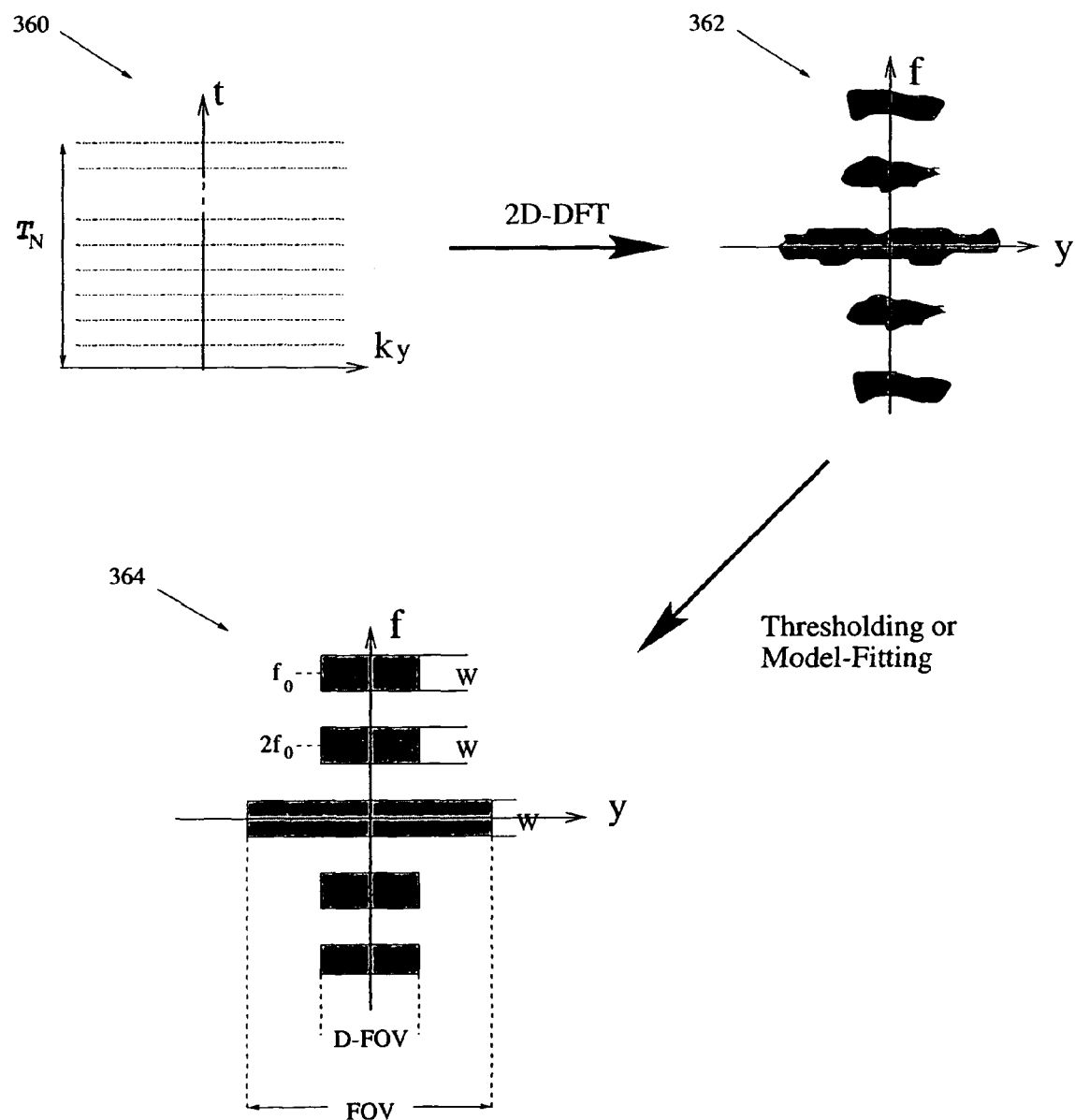
FIG. 12 is a graphic illustration of the data processing steps that are used to derive the DKT support of the imaged object from MR data acquired during a prescan stage that forms part of the scanning method of FIG. 8.

FIG. 5 shows a sampling schedule $\Psi^{DMA}$ that is used to estimate the required DKT supports by sequentially estimating the marginal DKT supports. In FIG. 5 a point at ($k_x^0$,t) indicates an MR acquisition at time $t_0$ of a line in k-space with $k_y$ being the readout direction and $k_x^0$ being the sampling location in the phase-encode direction. As seen from the figure, we acquire such k-space data for a fixed $k_x^0$ at a temporal constant rate, over a period of time, TN, sufficient to obtain an estimate of the DKT support. For a heart beating at 1 Hz, we may need to acquire such navigator data for a few tens of seconds. This acquisition then provides us with the data set $\{I(k_x,k_y,t)\}_{\Psi^{DMA}}$ (i.e. the values of the function $I(k_x,k_y,t)$ sampled according to the DMA sampling schedule $\Psi^{DMA}$). Panel 360 of FIG. 12 illustrates the data that is acquired for a fixed $k_x$-sample location ($k_x^0$). We take a 2D Fourier transform of this data (w.r.t. $k_y$ and t; for $k_x=k_x^0$), to obtain the DKT function $g_0(y,f)$, and threshold the result, in order to obtain the marginal DKT support estimate $\beta_I(k_x^0)$ shown in panel 364. The thresholding removes the artifacts in the DKT support due to the subject's breathing during the MR data acquisition.

Instead of thresholding, we can also fit a parametric model to the support of the data shown in panel 362, to compute the DKT support model parameters. For instance, the marginal DKT support may be characterized in terms of the dimensions of the FOV (FOV), the dimensions of the dynamic FOV (DFOV), the harmonic frequency ($f_0$), width of harmonic bands (w), and number of significant harmonic bands (2h+1). Then for a measured DKT function $g_0(y,f)$, the marginal DKT support to be used in the model can be found by solving the following optimization problem:

$$\operatorname*{argmin}_{\mathcal{B}(FOV,DFOV,f_0,h,w)} E_{\mathcal{B}}(g_0(y, f)) + c(\mathcal{B}) \quad \text{Eq. (28)}$$

where $\beta(\cdot)$ defines the DKT support for a given set of parameters (FOV,DFOV,$f_0$,h,w); the quantity $E_\beta(g_0(y,f))$ measures the energy of $g_0(y,f)$ contained within the set $\beta$; and $c(\beta)$ penalizes the size of the set $\beta$, for instance by measuring its area. Such an optimization problem can be solved numerically in order to compute the marginal DKT support. Minimizing the quantity in Eq. (13) provides an estimate of the DKT support that balances two conflicting aspects: (i) the match to the measured DKT function $g_0(y,f)$; and (ii) the cost $c(\beta)$, which may be related to, for instance, the required $T_R$ for a valid sampling schedule for an object with DKT support $\beta(\cdot)$. By giving up a little on the fit to $g_0(y,f)$, the artifacts introduced into the reconstruction will have a small non-zero energy, but the requirements on $T_R$ may be advantageously relaxed. Furthermore, because $g_0(y,f)$, is only an estimate, possibly contaminated by respiratory artifacts, a perfect fit to $g_0(y,f)$, is not desired. It is also clear that there is great flexibility available in the choice of the energy function $E_\beta(\cdot)$, and cost function $c(\beta)$, that can be used to tailor the optimization problem and resulting tradeoff to the particular application.

Recall that the DMA can be acquired at multiple sampling locations in $k_x$. By computing the 2D Fourier transform of the data (w,.r,.t. $k_y$, and t) acquired for each of these sampling locations we obtain a series of DKT functions $g_0(y,f),g_1(y,f), \ldots, g_n(y,f)$. We can form a joint estimate of the DKT support to be used in the model, by solving the following modified version of optimization problem outlined in Eq. (28):

$$\operatorname*{argmin}_{\mathcal{B}(FOV, D-FOV, f_0, h, w)} \sum_{n=0}^{N} \lambda_n E_{\mathcal{B}}(g_n, (y, f)) + c(\mathcal{B}) \quad \text{Eq. (29)}$$

where the parameters $\lambda_n$ can be used to weigh the influence of the different $k_x$ sample locations. This approach can provide better estimates of the DKT support albeit at the cost of increased prescan time requirement.

In another embodiment shown in FIG. 11(b), we use an MR localizer scan to estimate the spatial components of the DKT support model i.e. the FOV and the D-FOV. These parameters can be derived from the localizer scan by automatically segmenting the dynamic cardiac region in the field-of-view or can be manually marked by the MR operator. ECG data for the subject is also collected and its temporal Fourier transform is used to estimate the temporal components of the DKT support model, namely ($f_0$, h, w). Estimates of the significant number of harmonics and width of harmonic bands may rely on previously tabulated data-bases which correlate these quantities to the measured ECG spectrum and results of the localizer scan.

The third method for computing the DKT support includes respiratory adaptation of the DMA-sampling schedule $\Psi^{DMA}$. This embodiment is shown in FIG. 11(c). As a first step, we decide in block 320 whether we need to collect new respiratory navigator data in order to estimate the current diaphragm displacement. At the first pass through the loop the answer is clearly yes; at subsequent passes the answer will be decided based on the respiratory update rate computed earlier. If respiratory navigator is to be acquired, we determine the current diaphragm position ($d_0$) by performing a navigator pulse sequence 322. The respiratory phase is then updated in block 324, based upon the newly acquired respiratory navigator data; or in case new respiratory navigator data has not been acquired, by extrapolating from previous respiratory phase values.

The updated respiratory phase (diaphragm displacement d0), is used in conjunction with the respiratory compensation table to compute the corresponding respiratory motion parameters P(t) and q(t). These motion parameters are used to adapt the next acquisition directed by the DMA schedule $\Psi^{DMA}$ according to the adaptation strategy prescribed in (B1)-(B3). The collected data is processed in 334 as illustrated in FIG. 12 and the DKT support 364 is estimated by solving the optimization problem of Eq. (28) or Eq. (29). For this particular embodiment, since we prospectively compensate for the respiratory motion, the data-set in panel 360 (of FIG. 12) will have reduced respiratory artifacts and it may be simpler to estimate the DKT support. Hence we can trade increased acquisition complexity for decrease in the processing required for DKT support estimation.

The final step in the prescan process 250 of FIG. 8 is step 256, in which the optimal time-sequential sampling schedule is calculated and stored in the sampling schedule 258. We use the estimated DKT support $\beta_I$ at this stage to determine the sampling schedule. The sampling schedule also depends upon the desired image resolution along the phase-encode direction.

TS SAMPLING SCHEDULE DESIGN: In general the TS sampling schedule 258 contains information about: (1) time-instants at which MR data is acquired; (2) the slice that is excited and k-space point or trajectory sampled at each of those time-instants. In the preferred embodiment (spinwarp imaging of a single 2D slice) the sampling schedule is a list that indicates the order in which the $k_y$ phase encodings are to be applied when acquiring image data from the subject of the examination and the time instants at which each view should be acquired. Recall that the same k-space location may be sampled multiple times at different acquisition time instants, the number of repetitions determined by considerations including: final image accuracy, shape of the DKT support (in particular width of the bands), and limits on acquisition time. Since a single slice is being imaged, the parameters $(B(n), \mu(n), \mu_0(n))$ that define the slice that is to be excited remain the same (i.e., independent of n) for all sampling instants in the TS sampling schedule. We now describe how the TS sampling schedule is designed based on the previously estimated DKT support $\beta_I$ and the desired spatial resolution.

Following the time-sequential sampling theory, as presented in "Lattice Theoretic Analysis of time-sequential sampling of spatio-temporal signals, Part I", by N. P. Willis and Y. Bresler, IEEE Transactions of Information Theory, vol 43, pp 190-207, 1997, we search for sampling schedules that lie on a (rational) $(k_y, t)$ lattice $\Lambda A$, defined as follows:

$$\Lambda_A = \left\{ (k_y, t): \begin{bmatrix} k_y \\ t \end{bmatrix} = Am; m \in \mathbb{Z}^2 \right\} \qquad \text{Eq. (30)}$$

where $\mathbb{Z}$ denotes the set of integers and $A \in \mathbb{R}^{2 \times 2}$ (referred to as the basis of the lattice $\Lambda_A$) is an upper triangular matrix of the following form:

$$A = \begin{bmatrix} a_{11} & a_{12} \\ 0 & a_{22} \end{bmatrix} \qquad \text{Eq. (31)}$$

For a lattice $\Lambda_A$, a polar lattice $\Lambda_A^*$ is defined as the lattice whose basis is the matrix $A^{-T}$ (i.e transposing the matrix A and then forming its inverse). When the signal I(ky,t) (with DKT support $\beta_I$) is sampled on the lattice $\Lambda_A$ (i.e. we compute the value of the signal $I(k_y, t)$ for the set of points $(k_y, t) \in \Lambda_A$), the DTFT of the sampled signal (i.e. $\{I(k_x, k_y, t)\}_{\Lambda_A}$) consists of (scaled) translates of the original spectrum in (y,f) (i.e. I(y,f)) replicated on points of the polar lattice $\Lambda_A^*$. Thus in order to recover the signal $I(k_y, t)$ from its samples, without aliasing artifacts, we need the following conditions to be satisfied by the sampling lattice:

C1. The sampling lattice $\Lambda_A^*$ should pack the DKT support $\beta_I$, i.e replicas of the DKT support $\beta_I$ replicated on the points of the lattice $\Lambda_A^*$ should not overlap.

As long as the sampling lattice $\Lambda_A^*$ satisfies the condition (C1), we will be able to reconstruct the original TVI from the samples obtained at the sampling locations defined by the lattice. However this sampling schedule will not satisfy the time-sequential sampling constraint that restricts us to acquiring only one phase-encode line at a given time-instant. To account for this additional constraint, we first note that in order to reconstruct the TVI to a given spatial resolution, we need to acquire MR data only for a certain set of phase-encodes $\kappa$. In general the frequencies in set $\kappa$ need not be contiguous, but for clarity we discuss the special case in which $\kappa$ is defined by a range of spatial frequencies $\kappa = [k_{y,min}, k_{y,max}]$ and furthermore $k_{y,min} = -k_{y,max}$. We then define a sampling schedule determined by a lattice $\Lambda_A^*$, and the desired phase-encode range, as follows:

$$\Psi_A^\kappa = \{(k_y, t): (k_y, t) \in \Lambda_A, k_y \in \kappa\} \qquad \text{Eq. (32)}$$

i.e. we acquire data for only those set of phase-encodes which fall within the range determined by the required spatial resolution.

In order for the sampling schedule $\Psi_A^\kappa$ to satisfy the time-sequential constraint, we need the lattice with the basis matrix $[a_{11}] \in \mathbb{R}^{I \times 1}$ to pack the set $\kappa$. This can be shown to be equivalent to the condition $a_{11} \geq 2k_{y,max}$. Furthermore, if we choose $a_{11} = 2k_{y,max}$ then the resulting sampling schedule will indicate acquisition of data at a constant temporal rate i.e. fixed $T_R (=a_{22})$.

Now our task is to find $a_{12}, a_{22}$ (or $T_R$), such that condition (C1) is satisfied, i.e. the lattice with basis matrix $$A^* = A^{-T} \qquad \text{Eq. (33)}$$
$$= \begin{bmatrix} 1/2k_{y,max} & 0 \\ -a_{12}/(2k_{y,max}T_R) & 1/T_R \end{bmatrix}$$
$$= \begin{bmatrix} 1/2k_{y,max} & 0 \\ b_{21} & b_{22} \end{bmatrix}$$

packs the DKT support $\beta_I$. This is a geometric packing problem and we search for $b_{12}, b_{22}$ over a discretized grid such that this condition is satisfied. Furthermore we look for the smallest satisfactory value of $b_{22}$, so that the required temporal sampling rate is minimized (Note that $T_R = 1/b_{22}$).

Alternative optimality criteria and additional constraints can be applied while solving the above search problem to find an appropriate sampling lattice. For instance, we can pick the particular solution that maximizes the CNR (contrast to noise ratio) of the reconstruction, which depends upon the repetition time $T_R$. Furthermore the pulse sequence to be used for the image scan can itself be selected based upon the repetition time determined at this stage; or alternatively the choice of the repetition time and pulse sequence can be jointly optimized to maximize the resultant CNR. Several such alternatives should be obvious to one skilled in the art.

Given the optimally selected lattice, the sampling schedule can be determined through Eq. (32). This sampling schedule is guaranteed to satisfy the Time-Sequential sampling constraint and henceforth we refer to this schedule as the TS sampling schedule $\Psi^{TS}$.

In certain imaging scenarios, it may be desirable to have gaps in the TS sampling schedule, i.e. for certain $T_R$ intervals we do not need to acquire any phase-encoded data (for $k_y \in \kappa$). For instance, such gaps may then be used to acquire respiratory navigator data instead. We can form such schedules by intentionally selecting $a_{11} \geq 2k_{y,max}$ when we search for the lattice that packs the DKT support. The resultant sampling schedule may have a repetition time that is smaller than the one obtained without the intentional over-estimation of $a_{11}$; but it is also expected to contain gaps where it does not require us to acquire any phase-encoded data for certain integer multiples of $T_R$. By controlling how large a value we select for $a_{11}$, we can control the density and position of these gaps.

The gaps in the TS sampling schedule can be used to acquire respiratory navigator data, time-warp navigator data etc. Note that the pulse sequence used to acquire this data can be distinct from the imaging pulse sequence and its choice can be optimized based upon the repetition time determined by the sampling schedule design.

Figure 13:
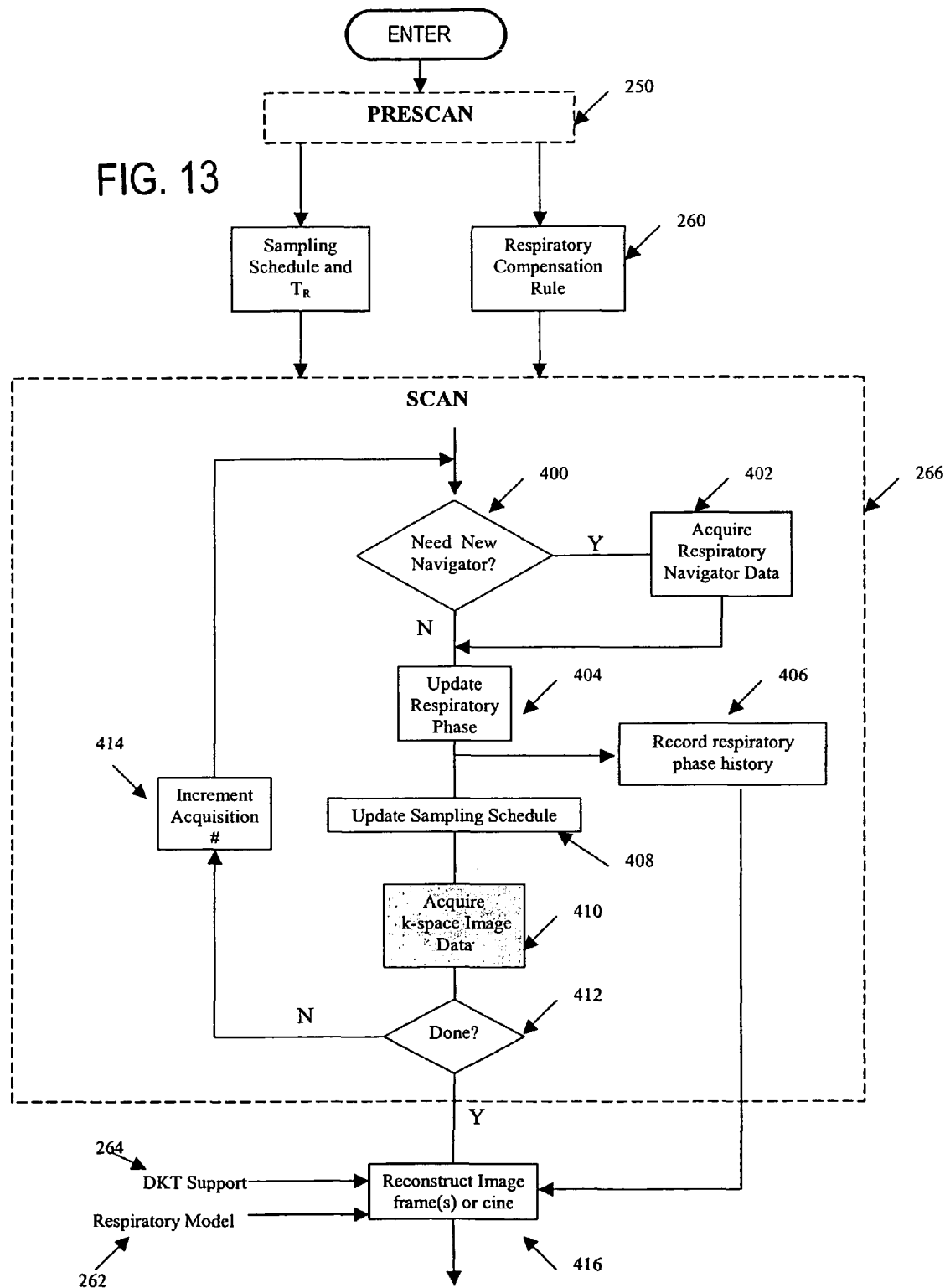
FIG. 13 is a flow chart of the steps in the image data acquisition stage, which forms part of the scanning method of FIG. 8.

IMAGING SCAN: Referring particularly to FIGS. 8 and 13, the image data acquisition step 266 is performed at the completion of the prescan step 250. The first step of the imaging scan, is to check at decision block 400 whether the respiratory phase used in compensation of the imaging pulse sequence needs a new measurement by a respiratory navigator. This check is based on information included in the sampling schedule as discussed above. If a new respiratory navigator is required, the subject's diaphragm position ($d_0$) is determined as indicated at process block 402. In the preferred embodiment this is accomplished by performing the same respiratory navigator pulse described above and used to build the respiratory compensation table 260. The respiratory phase is then updated in 404 based on the newly acquired navigator data or previously measured values of the respiratory phase. The current estimate of the respiratory phase is then recorded in a respiratory phase history as indicated at 406.

The updated respiratory phase (diaphragm displacement $d_0$), is used in conjunction with the respiratory compensation table to compute the corresponding respiratory motion parameters P(t) and q(t) for the current time.

Based on the TS sampling schedule and the estimated affine motion parameters, the MR data to be acquired at the next acquisition time instant is determined according to prescription (B1). Note that this is equivalent to an online update of the ACTS sampling schedule defined by Equation (5), i.e., even though we do not know a priori the ACTS sampling schedule for all acquisition time instants, we can compute the values in the schedule for the next sampling instant based on the previously computed TS sampling schedule and our estimate of the affine motion parameter values. This computation is done at process block 408 of FIG. 13.

One view of k-space data, as prescribed by the updated values in the ACTS sampling schedule, is then acquired as indicated at process block 410. This acquisition is done with the pulse sequence of FIG. 7 with its pulse-sequence parameters selected to acquire data as dictated by the adapted sampling schedule. In the laboratory frame of reference, the acquired data may correspond to an oblique slice, and the phase encode direction need not correspond to $k_y$. Additional Phase correction and/or Jacobian correction of the received signal may also be applied at this step, as prescribed by (B2)-(B3).

The scanning process continues until the last view is acquired as determined at decision block 412. As indicated above, the total number of views to be acquired is specified in the TS sampling schedule.

It should be apparent that other methods for measuring subject respiratory phase may be employed that do not require the acquisition of MR data. For example, a rubber bellows may be placed around the subject's thorax or abdomen and attached to a pressure transducer that records body motion due to breathing. If such a technique is to be used during the scan phase, it may also be used during the prescan phase to build the respiratory compensation table 260.

RECONSTRUCTION After the Imaging Scan 266 of FIG. 8, the desired image frame(s) or cardiac cine is reconstructed. As shown in process block 416 in FIG. 13, the reconstruction relies upon not only the acquired k-space image data, but also on the respiratory phase 406 recorded during the imaging scan; and on the DKT support 264 and the respiratory model obtained during prescan.

Figure 14A:
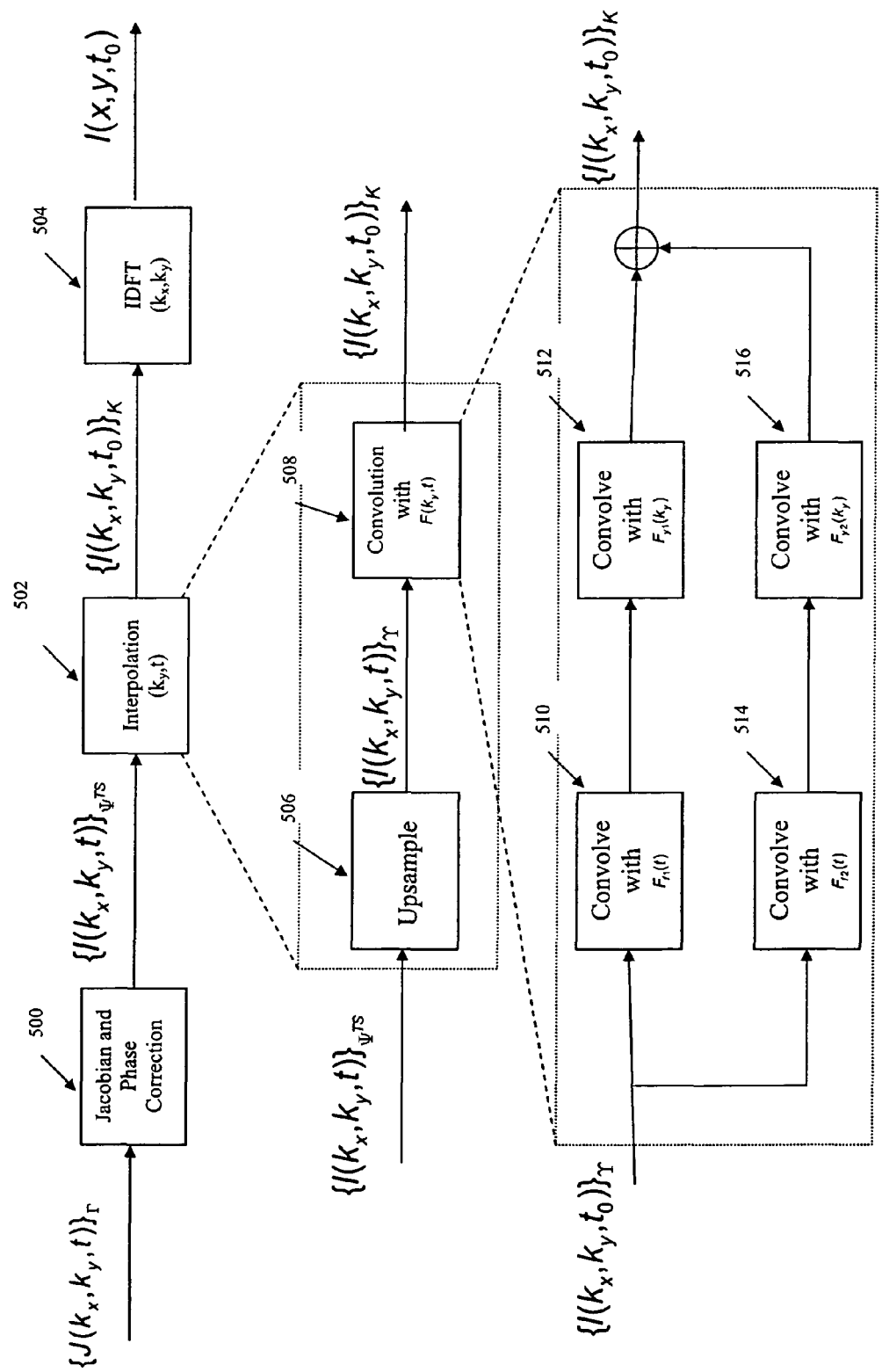
FIGS. 14A and 14B are flow charts of the steps in the image reconstruction phase, which forms part of the scanning method of FIG. 8.
Figure 14B:
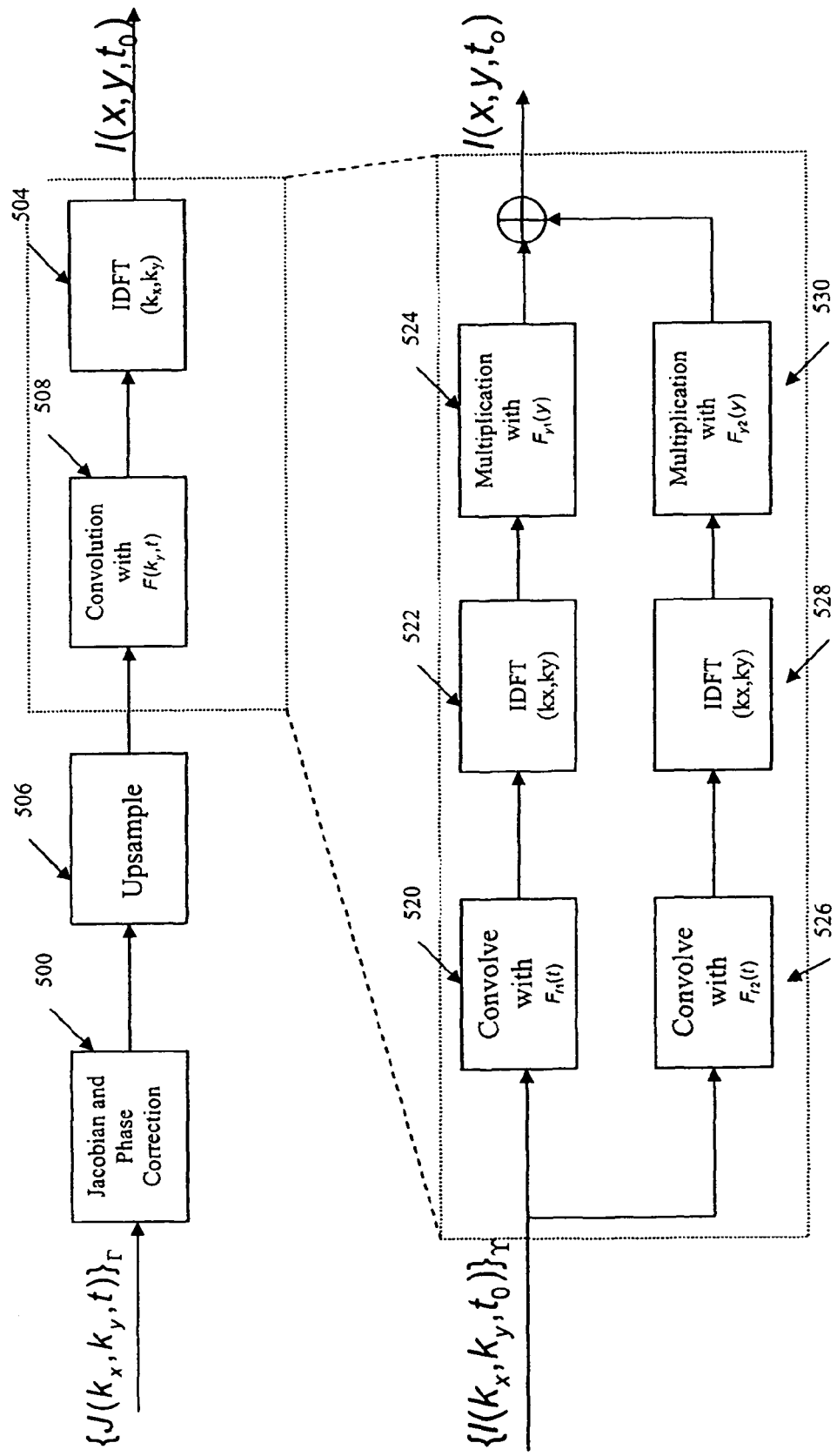
Figure 15A:
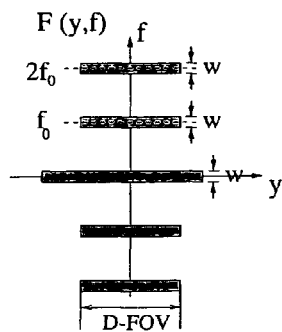
FIGS. 15A-15G are pictorial representations of the data processing performed on the acquired data as part of the image reconstruction step 268 of FIG. 8.
Figure 15B:
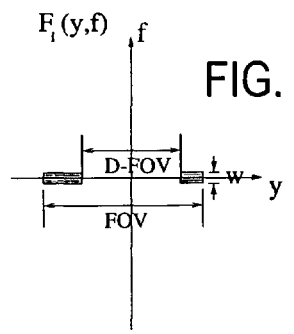
Figure 15C:
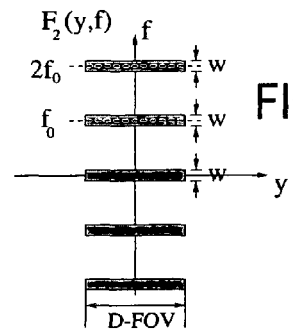
Figure 15D:
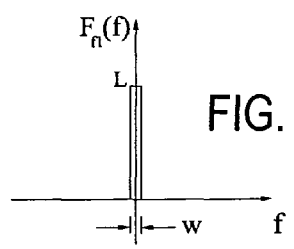
Figure 15E:
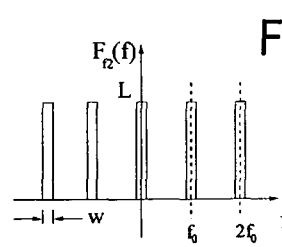
Figure 15F:
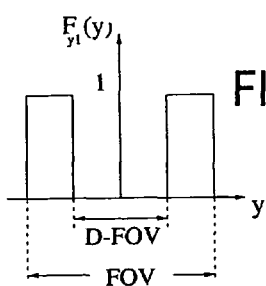
Figure 15G:
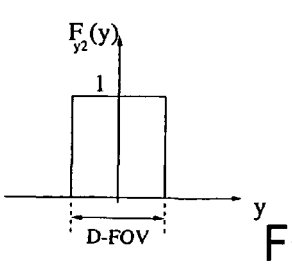

FIG. 14 shows a preferred embodiment of the method for reconstructing an image frame (at time $t_0$) from the acquired MR data. As discussed above, the acquired k-space image data represents samples of the imaged object $J(k_x, k_y, t)$ obtained at sample locations determined by the ACTS sampling schedule $\Gamma$ of Equation (5). As shown in process block 500, Jacobian and phase corrections are applied to this dataset according to prescription (B2)-(B3) in order to obtain k-space samples of the respiration-free object $I(k_x, k_y, t)$ at sample locations determined by the TS sampling schedule $\Psi^{TS}$.

In order to reconstruct the respiration free object I(x, y, t) at time $t_0$, at the desired resolution we interpolate the data to the grid $K_{t_0}$ in k-space:

$$K_{t_0} = \left\{ (k_x, k_y, t_0) : k_x = n_x/L_x, k_y = n_y/L_y; n_x = \frac{-N_x}{2}, \right.$$
$$\left. \frac{-N_x}{2}+1, \ldots, \frac{N_x}{2}; n_y = \frac{-N_y}{2}, \frac{-N_y}{2}+1, \ldots, \frac{N_y}{2} \right\}$$

where $L_x$, $L_y$ are the image field-of-view in the x and y-direction respectively and $N_x \times N_y$ is the desired image size. The interpolation is performed along all three axes $k_x$, $k_y$, and t as necessary to fill-in missing data values. The respiration-free image at time $t_0$, is reconstructed by computing the 2D-Inverse DFT of data interpolated to this finer grid at time $t_0$ as shown in process block 504. 504 in FIG. 14. The image of the actual object slice, depicting the effect of respiratory motion, can be reconstructed if desired by re-introducing the affine spatial co-ordinate transform as in Eq. (2). The affine motion parameters to be used are computed from the respiratory motion compensation table and knowledge of the respiratory phase at time $t_0$, recorded in the respiratory phase history.

FIG. 14 also shows certain linear-filtering based methods for interpolating the data to the desired finer grid $\kappa$ at time $t_0$. For instance, as shown in process block 506, we first upsample the data $I(k_x, k_y, t)$ from the coarse grid $\Psi^{TS}$ to a finer grid $\gamma$, defined as $$\gamma \triangleq$$
$$\{(k_x, k_y, t) : k_x = n_x/L_x, k_y = n_y/L_y, t = n_t T_R; n_x, n_y, n_t \in \mathbb{Z}\}$$

Eq. (34)

i.e. for points in ($k_x, k_y, t$) common to the two grids, we copy values from the coarser grid $\Psi^{TS}$ to the finer grid $\gamma$. The remaining points on the finer grid are assigned the value zero. The upsampled data is convolved with a 2D-linear shift-invariant filter with impulse response $F(k_y,t)$ to determine the value of $I(k_x,k_y,t)$ at time $t_0$, on the grid $K_{t_0}$ as shown in process block 508. The filter $F(k_y,t)$ ideally has frequency response $F(y,f)$ that has value 1 for $(y,f) \in \beta_I$ and zero outside as in FIG. 15(*a*) (where the DKT support $\beta_I$ is indicated by the shaded region). Practical filters can be constructed that approximate this ideal response as closely as desired In practice the filter length will be determined based on several factors, including the accuracy needed in the reconstructed image; the shape of the spatio-temporal spectral support (in particular the width of the bands); the length of time interval over which imaging data was acquired, available computational resources; and reconstruction time constraints.

There is considerable flexibility in the design of the linear filters that can be exploited to control different aspects of the reconstruction error or computational cost. For example, one can design the filters to control Gibb's ringing in the reconstruction.

The filtering operation in block 508, can be efficiently implemented as a parallel connection of separable 2D-filters with frequency responses $F_1(y,f)$ and $F_2(y,f)$, respectively as in FIGS. 15(*b*)-(*c*). Convolution with each of the 2D separable filters can be further reduced to a sequential cascade of 1-D convolutions with filters with impulse responses $F_i(k_y)$, $F_i(t)$ (i=1,2). This is shown in process blocks 510-516 in FIG. 14(*a*) and the corresponding ideal frequency responses of the 1D filters are shown in FIGS. 15(*d*)-(*g*).

A number of variations of the above described reconstruction process should be apparent. For instance, FIG. 14(*b*) shows another embodiment of the reconstruction process in which the convolution with the filters $F_i(k_y)$, has been replaced by multiplication by spatial window functions $F_i(y)$ (see FIGS. 15(*e*),(*g*)) by appropriately sequencing the IDFT and filtering operations.

In order to reconstruct the image frame at a particular time $t0$, the result of the convolution of the upsampled data with the filter $F(k_y,t)$ needs to be computed only for that particular time-instant. In order to reconstruct image frames at multiple time-instants or to create a cine reconstruction, the result of this convolution is computed at the relevant time-instants that correspond to each cine image frame.

Other embodiments of the reconstruction process need not involve linear filtering. For instance, in process block 502, of FIG. 14A, instead of interpolating the data using linear shift invariant filters, one can use parametric cardiac models of the sort described by, Eq. (19), to perform the interpolation.

The present invention may also be used with 2D and 3D projection, or radial sampling pulse sequences as described in U.S. Pat. Nos. 6,630,828 and 6,487,435. In spinwarp imaging, which has been described in detail above, k-space is sampled along lines parallel to the readout gradient axis. Data along each parallel k-space line is acquired almost instantaneously and is finely sampled. This reduces the sampling schedule design problem to that of determining the location, order and timing of applying the phase-encodes. In projection MR imaging, on the other hand, k-space data is acquired along radial lines passing through the origin in k-space. This trajectory in k-space is conveniently parameterized in terms of the variables $(\rho,\theta)$, where $\rho$ specifies the distance of a k-space point from the origin and $\theta$, is the angle that the line from the point to origin makes with the positive $k_x$-axis. Data along each radial k-space line (for a fixed $\theta$) is acquired almost instantaneously and is finely sampled. Thus, in this case, the sampling schedule design problem is reduced to optimizing the set of angles $\{\theta\}$, and the order and timing at which data is acquired. We now describe the modifications to be made to the adaptive imaging scheme described for spin-warp imaging to implement a second embodiment of the invention in which radial sampling is used. The steps in the radial imaging embodiment of the invention are again the ones shown in FIG. 8.

ESTABLISH RESPIRATORY MODEL The steps in this imaging phase remain unchanged from the ones described for the adaptive spin-warp imaging.

Figure 16:
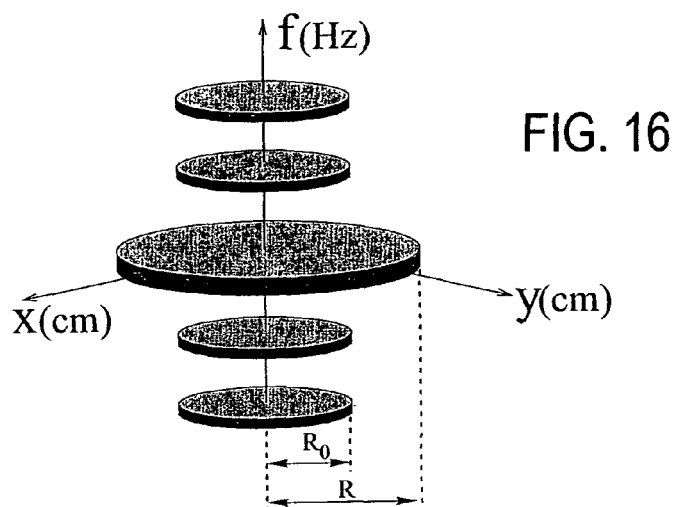
FIG. 16 is a graphic illustration of the banded spectral model, for a aperiodically beating heart.

ESTIMATING DKT SUPPORT The banded spectral model is illustrated in FIG. 16. For convenience of notation we illustrate the model with circular FOV and D-FOV (radius R and $R_0$ respectively). As described above, for projection imaging we acquire data along radial k-space lines, and we can ignore sampling effects along these radial lines. Since we therefore sample data in $(\theta,t)$, dimensions, we define the DKT support of the object in the $(k_\theta,f)$ domain, as follows:

$$\mathcal{B}_1 = \bigcup_\rho supp\{l(\rho, k_\theta, f)\} \qquad \text{Eq. (35)}$$

where, $k_\theta$ is the frequency variable corresponding to angle $\theta$.

Figure 17:
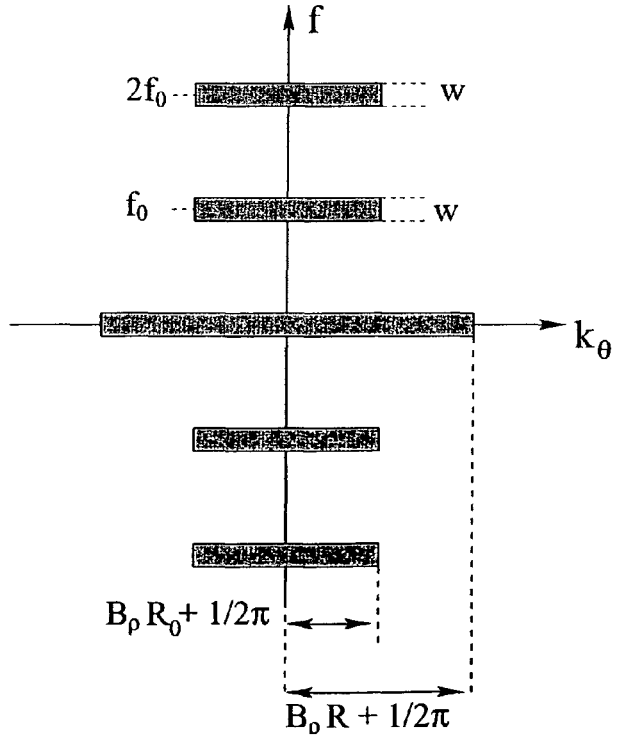
FIG. 17 is a graphic illustration of a dual-k-t support of a time-varying image of a aperiodically beating heart for projection MR imaging.

It can be shown, based on results derived in "Optical Scan for Time-Varying Tomography I: Theoretical Analysis and Fundamental Limitations" by N. P. Willis and Y. Bresler, in IEEE Transactions on Image Processing, vol 4, pp. 642-653, 1995, that this DKT support takes the form shown in FIG. 17. Note that in this support $B_\rho$, is a constant determined by the desired spatial resolution. From this we note that the DKT support defined above can be determined once we estimate the radii, R and $R_0$, of the FOV and DFOV along with the temporal spectral properties.

A method to determine these radii is to take a localizer prescan as shown in FIG. 11(*b*). The temporal spectral properties can be estimated from ECG data (as was described for adaptive spin-warp imaging earlier) and the information can be combined, in order to estimate the DKT support.

In order, to compute the DKT support from MR data (as was the case for the methods illustrated in FIGS. 11(*a*), (*c*)), we first note that by acquiring the data set illustrated in FIG. 5 and processing it according to the steps indicated in FIG. 12 (as described earlier), we can compute the extent of the FOV and DFOV along the y-axis. If we then repeat the process with the roles of $k_x$ and $k_y$ axis interchanged (i.e. with $k_x$ as the readout and $k_y$ as the phase-encode direction), we can determine the extent of the FOV and DFOV along the x-axis. From these we can compute values of the radii, R and $R_0$, of the circles in $(k_x, k_y)$ that would contain the FOV and DFOV respectively. Clearly the estimate can be made more accurate by repeating the DMA acquisition for other readout directions.

The MR acquisitions prescribed above can be adapted based on the subject's respiratory motion to yield a method to determine the DKT support, analogous to the one illustrated in FIG. 11(*c*).

TS SAMPLING SCHEDULE DESIGN As was mentioned above, for adaptive radial imaging, the sampling schedule indicates the position, order and timing at which we acquire data corresponding to angle $\theta$. Thus we search for sampling schedules that lie on a (rational) $(\theta,t)$ lattice $\Lambda_A$, defined as follows:

$$\Lambda_A = \left\{ (\theta, t) : \begin{bmatrix} \theta \\ t \end{bmatrix} = Am; \, m \in \mathbb{Z}^2 \right\} \quad \text{Eq. (36)}$$

where $\mathbb{Z}$ denotes the set of integers and $A \in \mathbb{R}^{2 \times 2}$ (referred to as the basis of the lattice $\Lambda_A$) is an upper triangular matrix of the following form:

$$A = \begin{bmatrix} a_{11} & a_{12} \\ 0 & a_{22} \end{bmatrix} \quad \text{Eq. (37)}$$

In order to reconstruct the cardiac TVI, we acquire samples along radial lines with the range of angles θ specified by κ=[0,π). This is the quantity analogous to the range of phase-encodes for which we acquire for adaptive spinwarp imaging.

With these definitions of the DKT support, $\beta_1$, and range of angles κ, the problem of designing the sampling schedule, reduces to one of finding the matrix A, with $a_{11} \geq \pi$, such that the lattice $\Lambda_A^*$ packs the DKT support $\beta_1$, This leads to the same computational problem as for adaptive spinwarp imaging and a solution is similarly found.

IMAGING SCAN The imaging scan step for projection imaging is similar to the one for adaptive spinwarp imaging except that the TS sampling schedule in this case indicates data acquisition along radial k-space lines instead of parallel k-space lines.

RECONSTRUCTION Once again, in order to reconstruct the TVI we interpolate the acquired data using the knowledge of the DKT support and then take DFTs (or IDFTs). However in this case the interpolation is done in the (ρ,θ,t) domain; and if shift-invariant linear filters are to be used, their frequency response is approximated to be unity over the estimated DKT support.

Figure 18A:
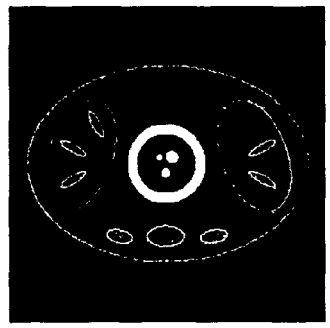
FIGS. 18A-18D show the results of a numerical experiment with a software cardiac phantom.
Figure 18B:
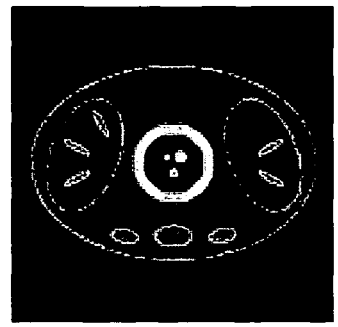

NUMERICAL EXPERIMENTS The preferred spinwarp MR imaging embodiment was tested using data generated from a dynamic software phantom. FIG. 18(a) is a 128*128 snapshot of the phantom. Cardiac motion was simulated by varying the diameter of the central disks in the image (representing the heart) as well as the positions and diameter of the three small features contained within the disks periodically at a frequency of 1 Hz. The initial test included only this cardiac motion; the rest of the FOV was static. The DKT support of the dynamic phantom was computed and the dynamic region was found to occupy roughly $\frac{1}{3}^{rd}$ of the FOV along y and about 95% of the dynamic energy was captured by the first 10 harmonic bands each of width 0.05 Hz. The TS sampling pattern for this DKT support was computed and the resultant $T_R$ was found to be 7.1 ms. Data for this sampling pattern was simulated in software for a total acquisition time of about 30 s and FIG. 18(b) shows a single frame from the reconstructed cine.

Figure 18C:
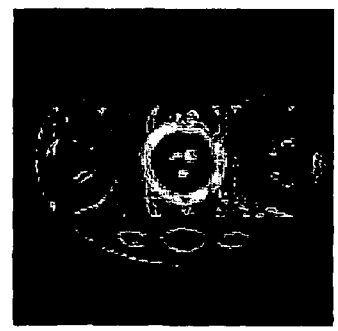
Figure 18D:
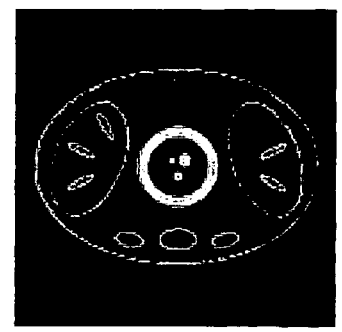

In the next set of simulations the effects of respiratory motion were added to the phantom. As discussed earlier, affine motion is a reasonable model for motion of the heart and adjoining structures in the FOV due to breathing. Therefore as an initial approximation, we assumed that in addition to the simulated cardiac motion described above, all structures within the FOV undergo affine respiration-induced motion. The parameters for the affine motion were chosen based on experimentally observed values as reported in "Model evaluation and calibration for prospective respiratory motion correction in coronary MR angiography based on 3-d image registration" by D. Manke, P. Rosch, K. Nehrke, P. Bornert and O. Dossel, published in IEEE Transactions on Medical Imaging, 2002, 21:1132-1141. The simulated respiratory rate was approximately 16 breaths/minute. MR data, as prescribed by the TS and ACTS sampling scheme was simulated for this scenario and FIGS. 18(c)-(d) show frames from the cines reconstructed using the two data sets. The reconstruction from the TS-sampled data shows blurring and ghosting artifacts due to the respiratory motion while the reconstruction from the ACTS-sampled data is essentially artifact free, demonstrating that the proposed scheme can perfectly compensate for respiratory motion when it is truly affine.

Figure 19:
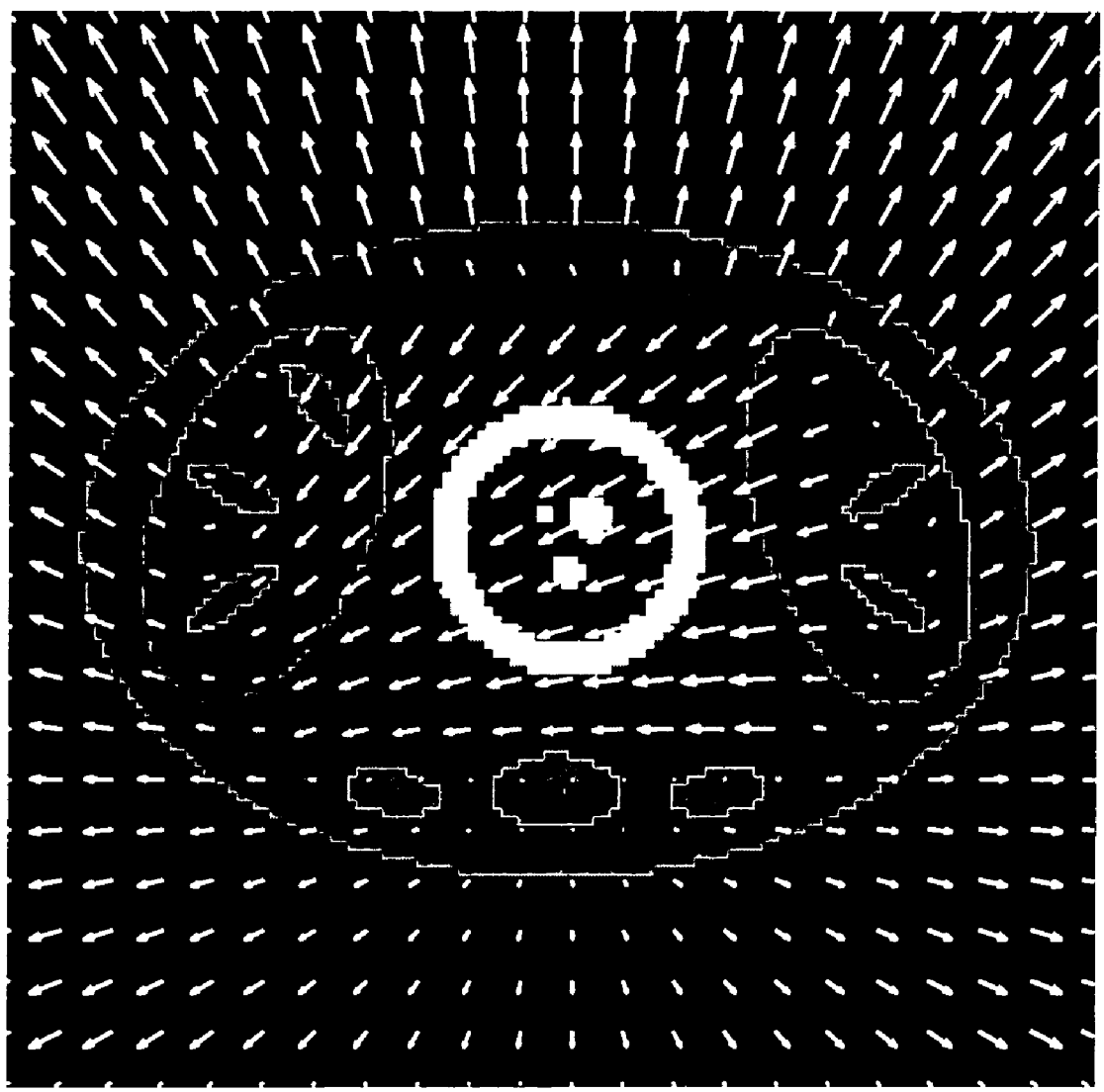
FIG. 19 shows the non-affine respiratory motion field at a particular time instant used in the numerical experiment.

The assumption that the entire imaged slice undergoes the same respiratory affine motion as the heart may not hold in practice. For example, the spine is relatively stationary during the breathing cycle. To account for this, we restricted the simulation of the affine motion as discussed above to the DFOV, while constraining a portion of the image (the bottom three ellipses in the frame shown representing the spine) to be still. The motion of boundary of the outer ellipse (representing the rib-cage) was simulated by expansion-contraction and displacement motion whose parameters were chosen to approximate physiologically reasonable values, as reported in "Chest wall motion during tidal breathing", by A. Groote, M. Wantier, G. Cheron, M. Estenne and M. Paiva, published in the Journal of Applied Physiology, 83(5):1531-1537, 1997. With these constraints on the respiratory motion of the DFOV, 'spine' and 'rib-cage', the motion-field was extended to the remainder of FOV so that it was smoothly spatially varying. The resultant motion-field at a given time-instant is shown in FIG. 19.

FIG. 20(a) shows two frames from a software phantom in which such a non-affine motion field was used to simulate respiratory motion in addition to the cardiac motion described earlier. The MR data acquisition process was simulated to acquire data for both the TS and ACTS sampling methods. The TS sampling sequence was designed using the same STS support as in the first set of simulations while the ACTS method was adapted based only on the knowledge of the affine motion in the DFOV which can be estimated using navigator data. Two frames from the corresponding reconstructed cines are shown in FIGS. 20(b)-(c).

Note that the ACTS reconstruction shown represents the estimate of I(r,t) (the underlying cardiac TVI without the respiratory motion) at the time instants of reconstruction and for comparison we show the true images for I(r,t) in FIG. 20(d). Though both imaging methods show image degradation due to the incorrect modeling of the respiratory motion, the ACTS reconstruction of the heart region itself (which may be of primary diagnostic importance) is clearly superior, as seen in FIG. 21, to the one obtained through the TS method.

The invention claimed is:

1. A method for acquiring and producing images of a time-varying subject with a magnetic resonance imaging (MRI) system, the steps comprising:
 a) performing a prescan of the time-varying subject that includes:
  a)i) estimating a dynamic model for the time-varying subject;
  a)ii computing a dynamic sampling schedule using the estimated dynamic model, the sampling schedule including information indicative of locations in k-space, and an order and timing in which the locations in k-space are to be sampled; and
  a)iii selecting a pulse sequence for directing the MRI system to acquire k-space image data from the time-varying subject;
 b) performing a scan of the time-varying subject to acquire k-space image data with the MRI system that includes:

b)i acquiring information indicative of the motion of the subject caused by respiration;

b)ii altering during the scan one of the information in the dynamic sampling schedule indicative of the locations in k-space, the order in which the locations in k-space are sampled, and the timing in which the locations in k-space are sampled, or the selected pulse sequence to compensate for respiratory motion of the subject; and b)iii acquiring k-space image data with the MRI system using the sampling schedule and the selected pulse sequence; and c) reconstructing an image using k-space image data acquired in step b).

2. The method as recited in claim 1 wherein the dynamic model in step a)i includes information about the dual-k-t support of the time-varying subject.

3. The method as recited in claim 1 in which during the pre-scan, step a)i includes acquisition of data with the MRI system.

4. The method as recited in claim 3 which further includes altering the data acquisition during the pre-scan to compensate for respiratory motion of the subject.

5. The method as recited in claim 1 in which the dynamic sampling schedule calculated in step a) includes information that enables additional reference data to be acquired with the MRI system during step b).

6. The method as recited in claim 5 in which step b) includes acquiring reference data with the MRI system that includes subject motion information.

7. The method as recited in claim 1 in which step a)i includes producing a respiratory motion calibration rule that relates motion of the subject to respiratory phase, step b)i) includes estimating the respiratory phase, and step b)iii) employs the respiratory phase and the respiratory motion calibration rule to determine the alteration.

8. The method as recited in claim 7, in which the respiratory motion calibration rule depends on the state of the time-varying subject.

9. The method as recited in claim 1, in which the selected pulse sequence directs the MRI system to sample k-space image data along parallel lines in k-space.

10. The method as recited in claim 1, in which the selected pulse sequence directs the MRI system to sample k-space image data along radial lines in k-space.

11. The method as recited in claim 1 in which the information acquired in step b)i) is indicative of an affine component of the respiratory motion of the subject.

12. The method as recited in claim 1, in which step b)i) further includes acquiring information indicative of subject motion not caused by respiration.

13. The method as recited in claim 1 in which step a) includes producing subject respiration information, and step b)i) is performed at times during the scan determined by said respiration information.

14. The method as recited in claim 1 in which the dynamic model estimated in step a) is used in the image reconstruction in step c).

15. The method as recited in claim 1 in which the time-varying subject is a beating heart.

16. A method for acquiring and producing an image of a time-varying subject with a magnetic resonance imaging (MRI) system, the steps comprising:

a) performing a prescan of the time-varying subject that includes:

a)i) estimating a dynamic model for the time-varying subject;

a)ii producing a dynamic sampling schedule using the estimated dynamic model, the dynamic sampling schedule including information indicative of locations in k-space, and an order and timing in which the locations in k-space are to be sampled;

b) performing a scan of the time-varying subject to acquire k-space image data using the MRI system that includes:

b)i acquiring information indicative of the motion of the subject caused by respiration during the scan;

b)ii acquiring k-space image data with the MRI system in accordance with the dynamic sampling schedule; and c) reconstructing an image, in which the motion of the subject caused by respiration during the scan is substantially compensated for, using the k-space image data acquired in step b)ii) and the subject motion information acquired in step b)i).

17. The method as recited in claim 16 wherein the dynamic model in step a)i includes information about the dual-k-t support of the time-varying subject.

18. The method as recited in claim 16 in which step a)i includes acquiring MR data with the MRI system.

19. The method as recited in claim 16 in which the dynamic sampling schedule includes information that enables additional reference data to be acquired with the MRI system during step b).

20. The method as recited in claim 19 in which step b) includes acquiring reference data with the MRI system that includes subject motion information.

21. The method as recited in claim 16 in which step a)i) includes producing a respiratory motion calibration rule that relates motion of the imaged subject to respiratory phase, step b)i) includes estimating the respiratory phase, and step c) employs the respiratory phase and the respiratory motion calibration rule during the image reconstruction.

22. The method as recited in claim 21, in which the respiratory motion calibration rule depends on the state of the time-varying subject.

23. The method as recited in claim 16, in which the k-space image data is acquired with a pulse sequence that samples k-space along a plurality of parallel lines in k-space.

24. The method as recited in claim 16, in which the k-space image data is acquired with a pulse sequence that samples k-space along a plurality of radial lines in k-space.

25. The method as recited in claim 16, in which step b)i) further includes acquiring information indicative of subject motion not caused by respiration.

26. The method as recited in claim 16 in which the dynamic model estimated in step a) is used in the image reconstruction in step c).

27. The method as recited in claim 16 in which the time-varying subject is a beating heart.

28. A method for acquiring and producing an image of a subject with a magnetic resonance imaging (MRI) system, the steps comprising:

a) selecting a pulse sequence and a sampling schedule for directing the MR system to acquire k-space image data from the subject by sampling k-space at designated times and k-space locations indicated by the sampling schedule;

b) performing a scan of the subject to acquire k-space image data with the MRI system that includes:

b)i acquiring information indicative of the motion of the subject caused by respiration;

b)ii acquiring k-space data by operating the MRI system with the selected pulse sequence and in accordance with the sampling schedule;

b)iii altering during the scan one of the information in the sampling schedule indicative of the k-space locations and the designated times at which the k-space locations are sampled, or the selected pulse sequence to compensate for respiratory motion of the subject;

c) producing corrected k-space image data by altering the acquired k-space data to compensate for volumetric changes in the subject caused by respiration, using the motion information acquired in step b)i; and d) reconstructing an image using the corrected k-space image data.

* * * * *